United States Patent
Abrams et al.

(10) Patent No.: US 10,131,901 B2
(45) Date of Patent: Nov. 20, 2018

(54) APPARATUSES, METHODS AND SYSTEMS FOR AUTOMATED PROCESSING OF NUCLEIC ACIDS AND ELECTROPHORETIC SAMPLE PREPARATION

(71) Applicant: SAGE SCIENCE, INC., Beverly, MA (US)

(72) Inventors: Ezra S. Abrams, Newton, MA (US); Danny Yun, S. Hamilton, MA (US); Todd J. Barbera, Marblehead, MA (US); Douglas Grosvenor Sabin, Marblehead, MA (US); T. Christian Boles, Bedford, MA (US)

(73) Assignee: SAGE SCIENCE, INC., Beverly, MA (US)

( * ) Notice: Subject to any disclaimer, the term of this patent is extended or adjusted under 35 U.S.C. 154(b) by 0 days.

(21) Appl. No.: 15/519,516

(22) PCT Filed: Oct. 15, 2015

(86) PCT No.: PCT/US2015/055833
§ 371 (c)(1),
(2) Date: Apr. 14, 2017

(87) PCT Pub. No.: WO2016/061416
PCT Pub. Date: Apr. 21, 2016

(65) Prior Publication Data
US 2017/0240882 A1    Aug. 24, 2017

Related U.S. Application Data

(60) Provisional application No. 62/064,454, filed on Oct. 15, 2014, provisional application No. 62/183,514, filed on Jun. 23, 2015.

(51) Int. Cl.
*G01N 27/447* (2006.01)
*C12N 15/10* (2006.01)
(Continued)

(52) U.S. Cl.
CPC ....... *C12N 15/101* (2013.01); *C12N 15/1017* (2013.01); *C12Q 1/6806* (2013.01);
(Continued)

(58) Field of Classification Search
CPC ....... G01N 27/44704; G01N 27/44743; G01N 27/44756; G01N 27/44778; G01N 27/453; C12M 47/06
See application file for complete search history.

(56) References Cited

U.S. PATENT DOCUMENTS 3,407,133 A    10/1968  Oliva et al.
3,533,933 A    10/1970  Strauch
(Continued)

FOREIGN PATENT DOCUMENTS

CN    102268426 A    12/2011
EP    0334615 A2    9/1989
(Continued)

OTHER PUBLICATIONS

International Search Report and Written Opinion, dated Feb. 2, 2016, for International Application No. PCT/US2015/055833.
(Continued)

*Primary Examiner* — Alexander S Noguerola
(74) *Attorney, Agent, or Firm* — Cooley LLP

(57) ABSTRACT

Methods, systems and apparatus for automated extraction, purification, and processing of nucleic acids from biological samples are presented. In some embodiments, hydrogel supports are used to immobilize particulate biological input samples and extract nucleic acids during operations. The use of hydrogel facilitates automated sample processing on robotic liquid handling systems. Devices, methods, and systems are also provided for electrophoretic sample preparation.

15 Claims, 26 Drawing Sheets

(51) Int. Cl.
  *C12Q 1/6806* (2018.01)
  *C12M 1/00* (2006.01)
(52) U.S. Cl.
  CPC . *G01N 27/44747* (2013.01); *G01N 27/44773* (2013.01); *G01N 27/44782* (2013.01); *C12M 47/06* (2013.01)

(56) References Cited

U.S. PATENT DOCUMENTS

| | | | |
|---|---|---|---|
| 3,616,454 A | 10/1971 | Levy et al. |
| 3,980,546 A | 9/1976 | Caccavo |
| 4,175,662 A | 11/1979 | Zold |
| 4,315,812 A | 2/1982 | Karlson |
| 4,375,401 A | 3/1983 | Catsimpoolas |
| 4,545,888 A | 10/1985 | Walsh |
| 4,608,147 A | 8/1986 | Clad |
| 4,655,898 A | 4/1987 | Poulhes et al. |
| 4,695,548 A * | 9/1987 | Cantor ............ G01N 27/44773 264/4.3 |
| 4,707,233 A | 11/1987 | Margolis |
| 4,708,782 A | 11/1987 | Andresen et al. |
| 4,834,862 A | 5/1989 | Breiner et al. |
| 4,835,263 A | 5/1989 | Nguyen et al. |
| 4,900,677 A | 2/1990 | Hewitt |
| 4,948,481 A | 8/1990 | Mullner |
| 5,062,942 A | 11/1991 | Kambara et al. |
| 5,169,511 A | 12/1992 | Allington et al. |
| 5,217,591 A | 6/1993 | Gombocz et al. |
| 5,242,568 A | 9/1993 | Her |
| 5,304,487 A | 4/1994 | Wilding et al. |
| 5,384,022 A | 1/1995 | Rajasekaran |
| 5,433,837 A | 7/1995 | Brunk et al. |
| 5,443,704 A | 8/1995 | Kirkpatrick et al. |
| 5,457,050 A * | 10/1995 | Mazurek ............ B29C 33/301 249/141 |
| 5,538,614 A | 7/1996 | Han |
| 5,707,812 A | 1/1998 | Horn et al. |
| 5,717,602 A | 2/1998 | Kenning |
| 5,800,690 A | 9/1998 | Chow et al. |
| 5,801,115 A | 9/1998 | Albers et al. |
| 5,804,684 A | 9/1998 | Su |
| 5,804,864 A | 9/1998 | Akiyama |
| 5,827,418 A | 10/1998 | Haven et al. |
| 5,840,169 A | 11/1998 | Andersen |
| 5,929,208 A | 7/1999 | Heller et al. |
| 6,290,831 B1 | 9/2001 | Liran et al. |
| 6,306,348 B1 | 10/2001 | Havens et al. |
| 6,319,472 B1 | 11/2001 | Ackley et al. |
| 6,344,325 B1 | 2/2002 | Quake et al. |
| 6,366,924 B1 | 4/2002 | Parce |
| 6,369,893 B1 | 4/2002 | Christel et al. |
| 6,388,746 B1 | 5/2002 | Eriksson et al. |
| 6,430,512 B1 | 8/2002 | Gallagher |
| 6,611,768 B2 | 8/2003 | Gallagher |
| 6,808,609 B1 | 10/2004 | Soane et al. |
| 6,834,240 B2 | 12/2004 | Gallagher |
| 6,867,851 B2 | 3/2005 | Blumenfeld et al. |
| 6,887,668 B2 * | 5/2005 | Liu ............ C12Q 1/68 204/450 |
| 6,919,571 B2 | 7/2005 | Lai et al. |
| 6,964,736 B2 | 11/2005 | Quake et al. |
| 7,056,746 B2 | 6/2006 | Seul et al. |
| 7,108,775 B2 | 9/2006 | Bahatt et al. |
| 7,122,104 B2 | 10/2006 | Cabilly et al. |
| 7,150,812 B2 | 12/2006 | Huang et al. |
| 7,413,642 B2 | 8/2008 | Hassard et al. |
| 7,419,784 B2 | 9/2008 | Dubrow et al. |
| 7,735,652 B2 | 6/2010 | Inglis et al. |
| 7,988,840 B2 | 8/2011 | Huang et al. |
| 8,361,298 B2 | 1/2013 | Sabin |
| 8,361,299 B2 | 1/2013 | Sabin et al. |
| 9,012,373 B2 | 4/2015 | Boles et al. |
| 9,599,590 B2 | 3/2017 | Sabin et al. |
| 9,719,961 B2 | 8/2017 | Sabin et al. |
| 2001/0000103 A1 | 4/2001 | Rhodes et al. |
| 2002/0076825 A1 | 6/2002 | Cheng et al. |
| 2002/0187503 A1 | 12/2002 | Harrold et al. |
| 2003/0151735 A1 | 8/2003 | Blumenfeld et al. |
| 2003/0170609 A1 | 9/2003 | Riqler |
| 2003/0190634 A1 | 10/2003 | Barany et al. |
| 2004/0011650 A1 | 1/2004 | Zenhausern et al. |
| 2004/0089546 A1 | 5/2004 | Bahatt et al. |
| 2004/0144651 A1 | 7/2004 | Huang et al. |
| 2005/0205427 A1 | 9/2005 | Boschetti et al. |
| 2006/0193752 A1 | 8/2006 | Levine |
| 2006/0223178 A1 | 10/2006 | Barber et al. |
| 2007/0284250 A1 | 12/2007 | Magnant et al. |
| 2007/0286773 A1 | 12/2007 | Schlautmann et al. |
| 2008/0023399 A1 | 1/2008 | Inglis et al. |
| 2008/0057557 A1 | 3/2008 | Margalit |
| 2008/0138809 A1 | 6/2008 | Kapur et al. |
| 2009/0241216 A1 | 9/2009 | Wang-pruski et al. |
| 2009/0308749 A1 * | 12/2009 | Park ............ G01N 27/44704 204/456 |
| 2010/0048412 A1 | 2/2010 | Liu et al. |
| 2010/0059414 A1 | 3/2010 | Sturm et al. |
| 2010/0126862 A1 | 5/2010 | Sabin et al. |
| 2010/0233693 A1 | 9/2010 | Kopf-Sill et al. |
| 2011/0062024 A1 | 3/2011 | Sabin et al. |
| 2011/0114487 A1 | 5/2011 | Schmidt et al. |
| 2011/0287436 A1 | 11/2011 | Shannon et al. |
| 2012/0195809 A1 | 8/2012 | Polwart et al. |
| 2013/0020199 A1 | 1/2013 | Margalit |
| 2013/0079251 A1 | 3/2013 | Boles et al. |
| 2013/0217022 A1 | 8/2013 | Cao et al. |
| 2013/0233714 A1 | 9/2013 | Sabin et al. |
| 2013/0240360 A1 | 9/2013 | Sabin et al. |
| 2014/0271602 A1 | 9/2014 | Zhang et al. |
| 2014/0284213 A1 | 9/2014 | Sabin et al. |
| 2015/0101932 A1 | 4/2015 | Sabin et al. |
| 2015/0166986 A1 | 6/2015 | Boles et al. |
| 2016/0370318 A1 | 12/2016 | Sabin et al. |
| 2017/0239658 A1 | 8/2017 | Abrams et al. |
| 2017/0254774 A1 | 9/2017 | Sabin et al. |

FOREIGN PATENT DOCUMENTS

| | | |
|---|---|---|
| EP | 0382426 A2 | 8/1990 |
| EP | 1384067 B1 | 1/2004 |
| GB | 2148325 A | 5/1985 |
| GB | 2148326 A | 5/1985 |
| JP | S62239047 A | 10/1987 |
| JP | S6322254 B2 | 5/1988 |
| JP | H07198680 A | 8/1995 |
| JP | 2000/224980 A | 8/2000 |
| JP | 2002/518672 A | 6/2002 |
| JP | 2002/310992 A | 10/2002 |
| JP | 2002/323477 A | 11/2002 |
| JP | 2004/510170 A | 4/2004 |
| JP | 2005/147957 A | 6/2005 |
| JP | 2005/532545 A | 10/2005 |
| WO | WO 1986/006743 A1 | 11/1986 |
| WO | WO 1996/004000 A1 | 2/1996 |
| WO | WO 1996/023213 A1 | 8/1996 |
| WO | WO 2002/028516 A1 | 4/2002 |
| WO | WO 2002/044706 A1 | 6/2002 |
| WO | WO 2003/087370 A1 | 10/2003 |
| WO | WO 2005/093388 A1 | 10/2005 |
| WO | WO 2006/031385 A2 | 3/2006 |
| WO | WO 2006/108101 A2 | 10/2006 |
| WO | WO 2008/016414 A2 | 2/2008 |
| WO | WO 2008/041718 A1 | 4/2008 |
| WO | WO 2010/042766 A1 | 4/2010 |
| WO | WO 2010/048605 A1 | 4/2010 |
| WO | WO 2012/171329 A1 | 12/2012 |
| WO | WO 2013/020089 A2 | 2/2013 |
| WO | WO 2014/059188 A1 | 4/2014 |
| WO | WO 2014/186819 A1 | 11/2014 |
| WO | WO 2016/061416 A1 | 4/2016 |
| WO | WO 2016/061556 A1 | 4/2016 |
| WO | WO 2017/087979 A1 | 5/2017 |
| WO | WO 2017/139669 A1 | 8/2017 |

(56) References Cited

FOREIGN PATENT DOCUMENTS

OTHER PUBLICATIONS

"ABI PRISM 377: DNA Sequencer." Perkin Elmer User's Manual, Part No. 903433, Rev. A. (1995):4-5-8-517.
Adey, et al., "In vitro, long-range sequence information for de novo genome assembly via transposase contiguity." Genome Research (2014); 24 (12): 2041-2049.
Amini, et al., "Haplotype-resolved whole genome sequencing by contiguity preserving transposition and combinatorial indexing." Nature Genetics (2014); 46 (12): 1343-1349.
Ansorge et al., "A simple field gradient technique which leads to sharpening of bands of DNA and to an increase in the number of receivable bases per gel", J. of Biochem. Biophys. Meth., 10:237-243 (1984).
Antunes, et al., "Targeted DNA excision in *Arabidopsis* by a re-engineered homing endonuclease." BMC Biotechnology (2012); 12: 86.
Australian Patent Examination Report No. 1 corresponding to Australian Application No. 2013329110, dated Jul. 28, 2016.
Bakajin, et al., "Separation of 100-kilobase DNA molecules in 10 seconds." Anal. Chem. (2001); 73 (24): 6053-6056.
Bibin, et al., "Depletion effects in binary hard-sphere fluids." J. Phys.: Condens. Matter, (1996); 8 (50): 10799-10821.
Bogdanove and Voytas, "TAL effectors: customizable proteins for DNA targeting." Science (2011); 333 (6051): 1843-1846.
Boncinelli et al., "An agarose gel resolving a wide range of DNA fragment lengths", Anal. Biochem., 134:40-43 (1983).
Boom et al. "Rapid and Simple Method for Purification of Nucleic Acids." J. Clin. Microbiol. 28.3(1990):495-503.
Borgström, et al., "Large scale library generation for high throughput sequencing." PLoS One (2011); 6 (4): e19119.
Chan et al., "DNA kinetics in microfabricated devices", Micro Electro Mechanical Systems, 60-63 (2002).
Chang et al., "New Mass-Spectrometry-Compatible Degradable Surfactant for Tissue Proteomics." J. Proteome Res. (2015); 14 (3): 1587-1599.
Chen et al., "An inexpensive microslab gel DNA electrophoresis system with real-time fluorescence detection", Electrophoresis, 27(2):387-393 (2006).
Cheng et al. "Interaction between DNA and Trimethyl-Ammonium Bromides with Different Alkyl Chain Lengths." Scientific World Journal Jan. 16, 2014, vol. 2014, No. 863409, pp. 1-9.
Chiu et al. "Differential Dependence on Chromatin Structure for Copper and Iron Ion Induction of DNA Double-Strand Breaks." Biochem. 34(1995):2653-2661.
Ciulla et al. "A Simple Method for DNA Purification from Peripheral Blood." Anal. Biochem. 174(1988):485-488.
Long, et al., "Multiplex genome engineering using CRISPR/Cas systems." Science (2013); 339 (6121): 819-823.
Cost, et al., "Directed assembly of DNA molecules via simultaneous ligation and digestion." BioTechniques (2007); 42(1): 84-89.
Costa et al., "Isolation of proteins and nucleic acids by electrophoresis on disposable gel columns", Electrophoresis, 17(4):781-783 (1995).
Cunha, et al., "Polymer-Mediated Compaction and Internal Dynamics of Isolated *Escherichia coli* Nucleoids." J. Struct. Biol. (2001); 136 (1): 53-66.
Davis, et al., "Deterministic hydrodynamics: taking blood apart." Proc. Natl. Acad. Sci. U.S.A. (2006); 103 (40): 14779-14784.
Diehl et al. "BEAMing: Single-Molecule PCR on Microparticles in Water-in-Oil Emulsions." Nat. Methods. 3.7(2006):551-559.
DNA Analysis, The Development of a Portable High-Speed DNA Analysis Device—Paving the Way Towards Point-Of-Care Diagnosis and Advanced Medical Treatment, http://www.azonano.com/Details.asp?Article ID=1783 (2006).
Duke, "Monte carlo reptation model of gel electrophoresis: steady state behavior." J. Chem. Phys. (1990); 93 (12): 9049-9054.
Duyster, et al., "Translocations involving anaplastic lymphoma kinase (ALK)" Oncogene (2001); 20 (40): 5623-5637.
Eckhardt, "A rapid method for the identification of plasmid desoxyribonucleic acid in bacteria." Plasmid (1978); 1(4): 584-588.
Esvelt et al., "Genome-scale engineering for systems and synthetic biology" Mol Syst Biol. (2013); 9:641.
Extended European Search Report for European Application No. 15851562.7 dated Jan. 29, 2018, 6 pages.
Full English language translation of Quan Du WO 2012/171329 A1, patent published Jun. 12, 2012, 54 pages.
Gardella, et al., "Detection of circular and linear herpesvirus DNA molecules in mammalian cells by gel electrophoresis." J. Virol. (1984); 50 (1): 248-254.
Gasiunas, et al., "Cas9-crRNA ribonucleoprotein complex mediates specific DNA cleavage for adaptive immunity in bacteria." ProcNatl Acad Sci U.S.A. (2012); 109 (39): E2579-2586.
Girvitz et al. "A rapid and efficient procedure for the purification of DNA from agarose gels", Analytical Biochemistry, 106(2):492-496 (1980).
Gnirke et al., "Solution hybrid selection with ultra-long oligonucleotides for massively parallel targeted sequencing." Nat Biotechnol. (2009); 27 (2): 182-189.
Goryshin et al. "Tn5 in vitro Transposition." J. Biol. Chem. 273. 13(1998):7367-7374.
Green et al. "Charting a Course for Genomic Medicine from Base Pairs to Bedside." Nature. 470(2011):204-213.
Griffin IV, et al. "In vitro Transposition of Tn552: A Tool for DNA Sequencing and Mutagenesis." Nucleic Acids Res. 27.19(1999):3859-3865.
Hamzah, "The effect of viscoelastic fluids on flows generated by spherical objects during sedimentation." PhD thesis, Massachusetts Institute of Technology, 2012, 27 pages.
Hanemaaijer et al. "Characterization of Clean and Fouled Ultrafiltration Membranes." Desalination, 68(1988): 93-108.
Heller et al., "Microelectrophoresis for the separation of DNA fragments", Electrophoresis, 13(1):512-520 (1992).
Hoffman, et al., "Hydrogels for biomedical applications." Advanced Drug Discovery Reviews (2002); 54: 3-12.
Hogan and Austin, "Importance of DNA stiffness in protein-DNA binding specificity." Nature (1987); 329 (6136): 263-266.
Holland, et al., "Isolation and characterization of a small catalytic domain released from the adenylate cyclase from *Escherichia coli* by digestion with trypsin." The Journal of Biological Chemistry (1988); 263 (29): 14661-14668.
Hsu et al., "Development and applications of CRISPR-Cas9 for genome engineering." Cell (2014);157 (6): 1262-1278.
Hsu, et al., "DNA targeting specificity of RNA-guided Cas9 nucleases." Nat Biotechnol. (2013); 31 (9): 827-832.
Huang, et al., "Continuous Particle Separation Through Deterministic Lateral Displacement." Science (2004); 304: 987-990.
Huang, et al., "A DNA prism for high-speed continuous fractionation of large DNA molecules." Nat. Biotechnol. (2002); 20 (10): 1048-1051.
Hughes, et al, "Expression profiling using microarrays fabricated by an ink-jet oligonucleotide synthesizer." Nat Biotechnol. (2001); 19(4): 342-347.
Inglis, et al., "Critical particle size for fractionation by deterministic lateral displacement." Lab Chip (2006); 6 (5): 655-658.
Inglis, et al., "Determining blood cell size using microfluidic hydrodynamics." J. Immunol. Methods (2008); 329 (1): 151-156.
Inoue et al., "I-shaped microchannel array chip for parallel electrophoretic analyses", Analytical Chemistry, 79:2168-2173 (2007).
International Preliminary Report on Patentability for International Application No. PCT/US2012/049603, dated Feb. 4, 2014.
International Preliminary Report on Patentability for International Application No. PCT/US2013/064403, dated Apr. 14, 2015.
International Preliminary Report on Patentability for International Application No. PCT/US2015/055833, dated Apr. 18, 2017.
International Preliminary Report on Patentability for International Application No. PCT/US2009/060065, dated Dec. 7, 2010.
International Preliminary Report on Patentability, dated Apr. 18, 2017, for International Application No. PCT/US2015/056104, 8 pages.
International Search Report and the Written Opinion for International Application No. PCT/US2013/064403, dated Jan. 24, 2014.

(56) References Cited

OTHER PUBLICATIONS

International Search Report and Written Opinion for International Application No. PCT/US2012/049603, dated May 17, 2013.
International Search Report and Written Opinion for International Application No. PCT/US2015/055833, dated Feb. 2, 2016.
International Search Report and Written Opinion, dated Dec. 11, 2017, for International Application No. PCT/US2017/055193.
International Search Report and Written Opinion, dated Feb. 8, 2010, for International Application No. PCT/US2009/060065.
International Search Report and Written Opinion, dated Feb. 12, 2016, for International Application No. PCT/US2015/056104.
International Search Report and Written Opinion, dated Feb. 3, 2017, for International Application No. PCT/US2016/063190.
International Search Report and Written Opinion, dated Jun. 27, 2017, for International Application No. PCT/US2017/017508.
Japanese Office Action dated Jun. 14, 2016 and corresponding to Japanese Application No. 2014-524127 (and English translation), 7 pages.
Jinek, et al., "A programmable dual-RNA-guided DNA endonuclease in adaptive bacterial immunity." Science (2012); 337 (6096): 816-821.
Johnson et al., "Sizing of DNA fragments by flow cytometry", Proc. SPIE, 1895:69-78 (1993).
Kaabouch et al., "An analysis system for DNA gel electrophoresis images based on automatic thresholding and enhancement", Electro/Information Technology, 2007 IEEE International Conference on May 17-20, 2007, pp. 26-31.
Karvelis, et al., "Programmable DNA cleavage in vitro by Cas9." Biochem Soc Trans. (2013); 41 (6): 1401-1406.
Khandurina et al., "Micropreparative Fraction Collection in Microfluidic Devices", Anal. Chem., 74(7):1737-1740 (2002).
Kumar et al., "Pyrrolidine Nucleic Acids: DNA/PNA Oligomers with 2-Hydroxy/Aminomethyl-4(thymin-1-yl)pyrrolidine-N-acetic acid", Organic Letters, 3(9):1269-1272 (2001).
Kunkel et al. "Analysis of Human Y-Chromosome-Specific Reiterated DNA in Chromosome Variants." PNAS. 74.3(1977):1245-1249.
La Spada and Taylor, "Repeat expansion disease: progress and puzzles in disease pathogenesis." Nature Reviews Genetics (2010); 11: 247-258.
Laemmli, "Cleavage of structural proteins during the assembly of the head of bacteriophage T4." Nature (1970); 227: 680-685.
Lagriffoul et al., "The Synthesis, Co-Oligomerization and Hybridization of a Thymine-Thymine Heterodimer Containing PNA", Bioorganic and Medical Chemistry Letters, 4:1081-1082 (1994).
Lam et al., "Genome mapping on nanochannel arrays for structural variation analysis and sequence assembly." Nat. Biotechnol. (2012); 30 (8): 771-776.
Ledford, Heidi, "AstraZeneca launches project to sequence 2 million genomes." Nature: International Weekly Journal of Science (2016); 532 (7600): 427.
Lerman, et al., "A transition to a compact form of DNA in polymer solutions." Proc. Nat. Acad. Sci. U.S.A. (1971); 68 (8):1886-1890.
Li et al., "A Simultaneous Space Sampling Method for DNA Fraction Collection Using a Comb Structure in Microfluidic Devices." Electrophoresis (2011); 32(23): 3392-3398.
Li et al., "On-chip fraction collection for multiple selected ssDNA fragments using isolated extraction channels." Journal of Chromatography A (2011); 1218(7): 997-1003.
Li et al., "Design of a PMMA Chip for Selective Extraction of Size-Fractioned DNA", Proceedings of the 1st IEEE International Conference on Nano/Micro Engineered and Molecular Systems, Zhuhai China, Jan. 18-21, 2006, pp. 105-109.
Li et al., "Design, simulation and optimization of a miniaturized device for size-fractioned DNA extraction", Electrophoresis (2007); 28(24):4661-4667.
Lin et al., "Addressable electric fields for size-fractioned sample extraction in microfluidic devices", Anal. Chem., 77(14):4338-4347 (2005).
Lin et al., "Selective extraction of size-fractioned DNA samples in microfabricated electrophoresis devices", Journal of Chromatography, 1010(2):255-268 (2003).
Liu et al., "DNA fragment analysis by an affordable multiple-channel capillary electrophoresis system", Electrophoresis, 24(1-2):93-95 (2003).
Liu et al., "pK-Matched Running Buffers for Gel Electrophoresis." Analytical Biochemistry (1999); 270(1): 112-122.
Loutherback, et al., "Deterministic microfluidic ratchet." Phys. Rev. Lett. (2009); 102 (4): 045301.
Loutherback, et al., "Deterministic separation of cancer cells from blood at 10 ml/min." AIP advances (2012); 2 (042107).
Loutherback, et al., "Improved performance of deterministic lateral displacement arrays with triangular posts." Microfluid. Nanofluid. (2010); 9 (6): 1143-1149.
Lundqvist et al., "Electrophoretic separation and confocal laser-induced fluorescence detection at ultralow concentrations in constricted fused-silica capillaries", Electrophoresis, 24(11):1737-1744 (2003).
Mali, et al., "RNA-guided human genome engineering via Cas9." Science (2013); 339 (6121): 823-826.
Margulies et al. "Genome Sequencing in Microfabricated High-Density Picolitre Reactors." Nature. 437.7057(2005):376-380.
Marshall et al., "Analytical micro-preparative electrophoresis: Quantitation of phosphoglucose isomerase isoenzymes", Anal. Biochem., 91(1):283-292 (1978).
Maydan, et al., "Electrophoretic High Molecular Weight DNA Purification Enables Optical Mapping." Boreal Genomics (2013); 1 page.
Meyer, et al., "Expanding Proteome Coverage with Orthogonal-specificity α-Lytic Proteases." Molecular & Cellular Proteomics (2014); 13 (3): 823-835.
Minalla et al., "Automated DNA fraction collection on glass microchips", Micro Total Analysis Systems, 2:946-948 (2002).
Morris, et al., "Fusion of a kinase gene, ALK, to a nucleolar protein gene, NPM, in non-Hodgkin's lymphoma." Science (1994); 263 (5151): 1281-1284.
Morton et al. "Crossing Microfluidic Streamlines to Lyse, Label and Wash Cells." Lab on a Chip. 8.9(2008):1448-1453.
New England_Restriction_Buffer, NEBuffer Performance Chart with Restriction Enzymes. 2013 [online]. [Retrieved on May 23, 2017]. Retrieved from the Internet: <URL: https://www.neb.com/-/media/NebUs/Files/nebuffer-performance-chart-with-restrictionenzymes.pdf>.
Nolin, et al., "Expansion of the Fragile X CGG Repeat in Females with Premutation or Intermediate Alleles." Am. J. Hum. Genet. (2003); 72 (2): 454-464.
Noolandi, and Chantal, In Methods in Molecular Biology vol. 12: Pulsed-field gel electrophoresis. Ed. Burmeister, Afargit, and Ulanovsky, Levy. Humana., pp. 73-103 and 135-143 (1992).
Olsen, et al., "Trypsin Cleaves Exclusively C-terminal to Arginine and Lysine Residues." Molecular & Cellular Proteomics (2004); 3: 608-614.
Olson, et al., "The structure of isometric capsids of bacteriophage t4." Virology (2001); 279 (2): 385-391.
Pamme, "Continuous flow separations in microfluidic devices." Lab Chip (2007); 7 (12): 1644-1659.
Pelletier, et al., "Physical manipulation of the *Escherichia coli* chromosome reveals its soft nature." Proc. Natl. Acad. Sci. U.S.A. (2012); 109 (40): E2649-E2656.
Persat et al., "Purification of Nucleic Acids from Whole Blood Using Isotachophoresis." Anal. Chem. (2009); 81 (22): 9507-9511.
Peterson et al., "Synthesis and oligomerization of Nα-Boc-Nα-(thymin-1-ylacetyl)ornithine", Bioorganic and Medical Chemistry Letters, 6:793-796 (1996).
Petty et al., "Characterization of DNA size determination of small fragments by flow cytometry", Anal. Chem., 67:1755 (1995).
Pluen, t al., "Diffusion of Macromolecules in Agarose Gels: Comparison of Linear and Globular Configurations." Biophysical Journal (1999); 77 (1): 542-552.
Rampino et al., "Apparatus for gel electrophoresis with continuous monitoring of individual DNA molecules by video epifluorescence microscopy", Anal. Biochem., 194(2):278-283 (1991).

(56) References Cited

OTHER PUBLICATIONS

Ren, et al., "A Simplified Method to Prepare PCR Template DNA for Screening of Transgenic and Knockout Mice." Journal of Biological Chemistry (2015); 290 45): 27248-27260.
Riehn et al. "Restriction Mapping in Nanofluidic Devices." PNAS. 102(2005):10012-10016.
Rittié and Perbal, "Enzymes used in molecular biology: a useful guide." Journal of Cell Communication and Signaling (2008); 2(1-2): 25-45.
Robertson et al. "Diffusion of Isolated DNA Molecules: Dependence on Length and Topology." PNAS. 103.19(2006):7310-7314.
Rothberg et al. "An Integrated Semiconductor Device Enabling Non-Optical Genome Sequencing." Nature. 475.7356(2011):348-352.
Scharenberg, et al., "Genome engineering with TAL-effector nucleases and alternative modular nuclease technologies." Curr Gene Ther. (2013); 13 (4): 291-303.
Schoch, et al., "Rapid and selective extraction, isolation, preconcentration, and quantitation of small RNAs from cell lysate using on-chip isotachophoresis." Lab on a Chip (2009); 9: 2145-2152.
Shalem et al, "Genome-scale CRISPR-Cas9 knockout screening in human cells." Science (2014); 343 (6166): 84-87.
SIGMA_P8340, Protease Inhibitor Cocktail for use with mammalian cell and tissue extracts. Catalog No. P8340. Sigma-Aldrich. 2010 [online]. [Retrieved on Mar. 20, 2017]. Retrieved from the Internet: <URL: https://www.sigmaaldrich.com/content/dam/sigmaaldrich/docs/Sigma/Datasheet/5/p8340dat.pdf>.
Singh-Gasson, et al, "Maskless fabrication of light-directed oligonucleotide microarrays using a digital micromirror array." Nat Biotechnol. (1999); 17 (10): 974-978.
Smith et al. "A Physical Map of the *Escherichia coli* K12 Genome." Science. 236.4807(1987):1448-1453.
Stoddard, et al., "Homing endonucleases: from microbial genetic invaders to reagents for targeted DNA modification." Structure (2011); 19 (1): 7-15.
Suh, E.R., et al., "Semi-automated quantification of C9orf72 expansion size reveals inverse correlation between hexanucleotide repeat No. And disease duration in frontotemporal degeneration." Acta Neuropathol (2015); 130(3): 363-372.
Sun et al., "Electrophoretic chip for high-fidelity fractionation of double-stranded DNA", Electrophoresis, 28(10):1572-1578 (2007).
Sutherland et al., "Electronic imaging system for direct and rapid quantitation of fluorescence from electrophoretic gels: application to ethidium bromide-stained DNA", Anal. Biochem., 163(2):446-457 (1987).
Tabak et al., "A method for the recovery of DNA from agarose gels", Nucleic Acids Research, 5(7): 2321-2332 (1978).
Tan, et al., "Gel Electrophoresis: DNA Science without the DNA!," Biochemistry and Molecular Biology Education (2007); 35 (5): 342-349.
Tarn, et al., "On-chip processing of particles and cells via multilaminar flow streams." Anal. Bioanal. Chem. (2014); 406: 139-161.
Tegenfeldt, et al., "The dynamics of genomic-length DNA molecules in 100-nm channels." Proc. Natl. Acad. Sci. U.S.A. (2004); 101 (30): 10979-10983.
Tomkinson, et al., "Location of the active site for enzyme-adenylate formation in DNA ligases." PNAS (1991); 88 (2): 400-404.
Urnov, et al., "Genome editing with engineered zinc finger nucleases." Nat Rev Genet. (2010); 11 (9): 636-646.
Volkmuth and Austin, "DNA electrophoresis in microlithographic arrays." Nature (1992); 358 (6387): 600-602.
Wang et al. " PacBio-LITS: a large-insert targeted sequencing method for characterization of human disease-associated chromosomal structural variations." BMC Genomics (2015); 16: 214.
Wang et al., "A simple microfluidic system for efficient capillary electrophoretic separation and sensitive fluorimetric detection of DNA fragments using light-emitting diode and liquid-core waveguide techniques", Electrophoresis (2005); 26(19):3602-3608.
Wang, et al., "Genetic screens in human cells using the CRISPR-Cas9 system." Science (2014); 343(6166): 80-84.
Wang, et al., "IRDL Cloning: A One-Tube, Zero-Background, Easy-to-Use, Directional Cloning Method Improves Throughput in Recombinant DNA Preparation." PLoS One (2014); 9(9): e107907.
Wang, et al., "Stretching DNA with optical tweezers." Biophys. J. (1997); 72 (3): 1335-1346.
Wilson, et al., "Engineered DNA ligases with improved activities in vitro." Protein Engineering, Design & Selection (2013); 26 (7): 471-478.
Worcel et al. "On the Structure of the Folded Chromosome of *Escherichia coli*." J. Mol. Biol. 71.2(1972):127-147.
Xiao et al., "CE with LED-based detection: An update", Electrophoresis, 30(1):189-202 (2008).
Zakharov et al., "Recovery of SDS-protein and DNA using commercial automated gel electrophoresis apparatus", Appl. Theor. Electrophor., 5(1):25-29 (1995).
Zalewski et al., "Electrokinetic sorting and collection of fractions for preparative capillary electrophoresis on a chip", Lab on a Chip (2008); 8 (5): 801-809.
Zaret et al. "Micrococcal Nuclease Analysis of Chromatin Structure." Curr. Protoc. Mol. Biol. S69(2005):21.1.1-21.1.17.
Zetsche et al., "Cpf1 is a single RNA-guided endonuclease of a class 2 CRISPR-Cas system." Cell (2015); 163 (3): 759-771.
Zimmerman and Minton, "Macromolecular crowding: biochemical, biophysical, and physiological consequences." Annu. Rev. Biophys. Biomol. Struct. (1993); 22 (1): 27-65.

\* cited by examiner

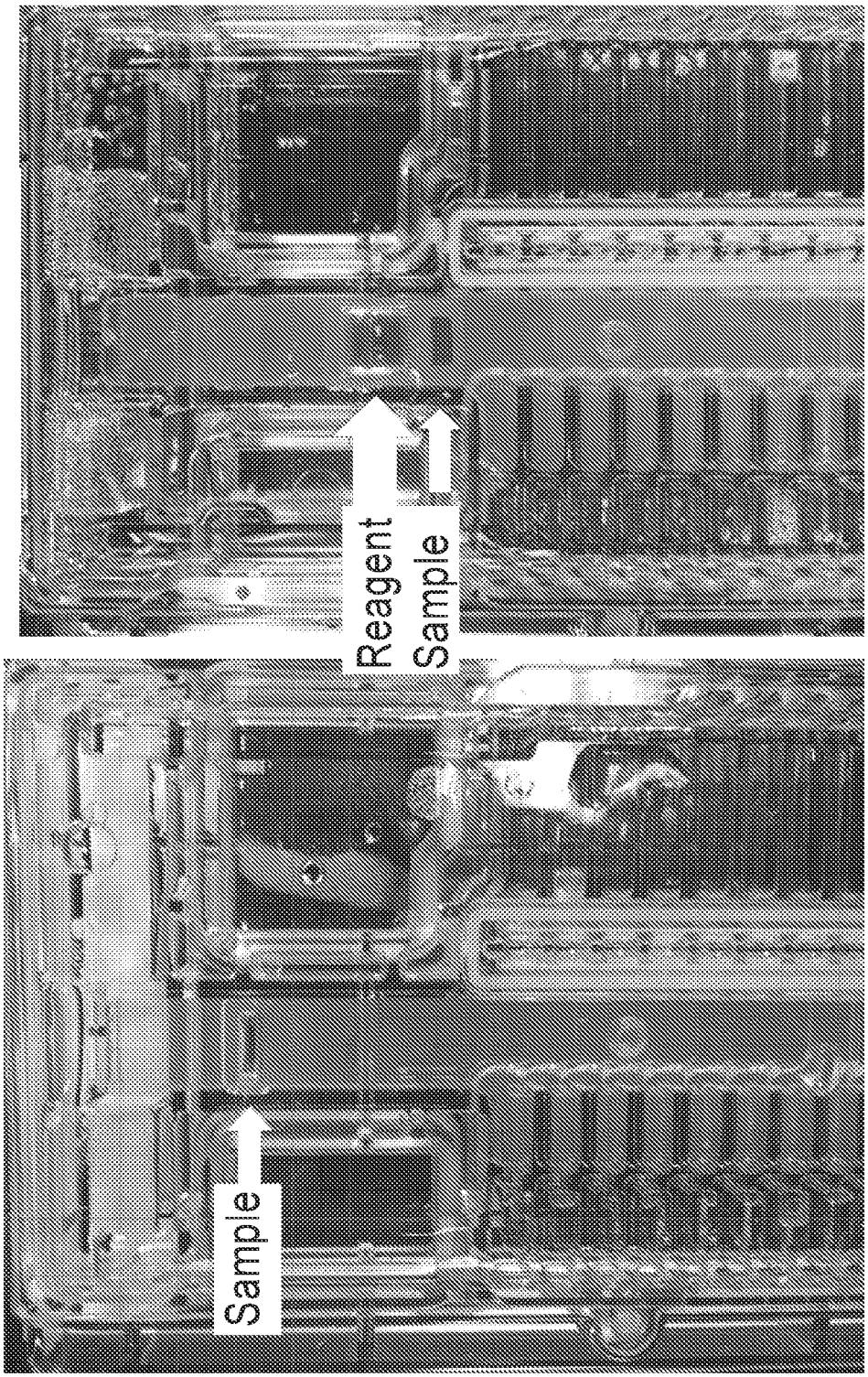

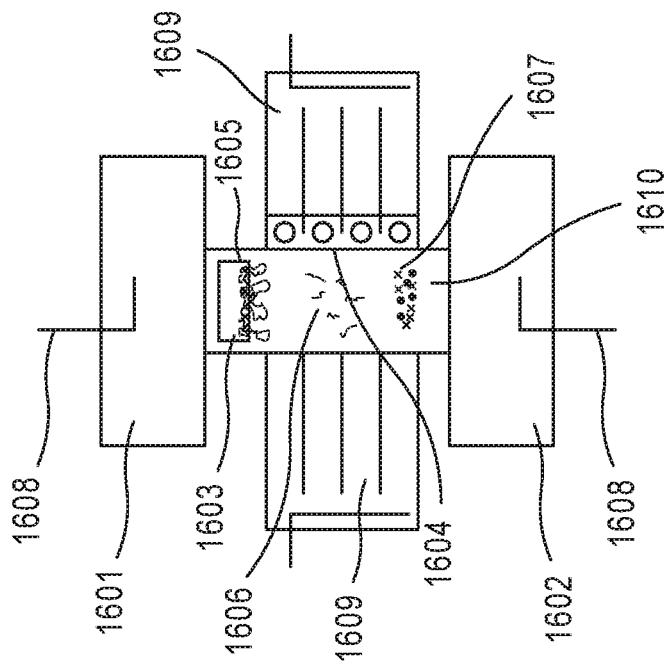
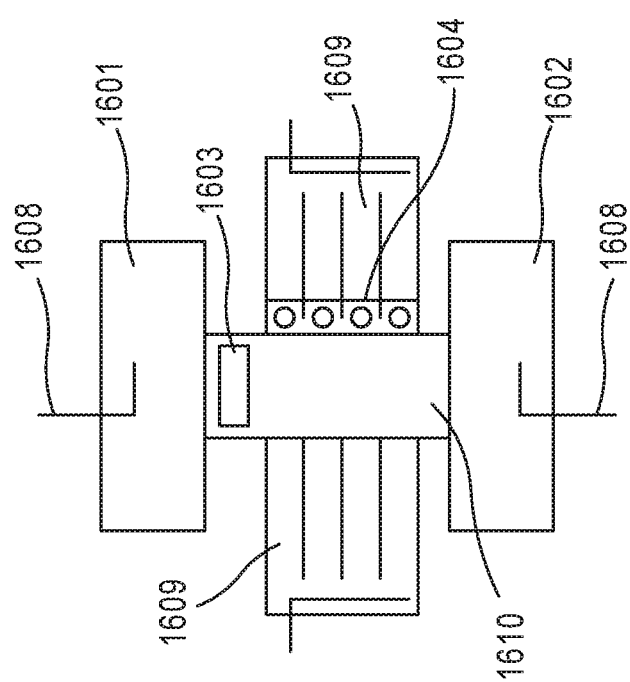

APPARATUSES, METHODS AND SYSTEMS FOR AUTOMATED PROCESSING OF NUCLEIC ACIDS AND ELECTROPHORETIC SAMPLE PREPARATION

CROSS-REFERENCE TO RELATED APPLICATIONS

This application claims priority to International Patent Application No. PCT/US2015/055833, filed Oct. 15, 2015, and entitled, "Apparatuses, Methods and Systems for Automated Processing of Nucleic Acids and Electrophoretic Sample Preparation," which claims priority to and benefit of U.S. Provisional Patent Application No. 62/064,454, filed Oct. 15, 2014, and entitled, "Apparatuses, Methods and Systems for Automated Processing of Nucleic Acids," and U.S. Provisional Patent Application No. 62/183,514, filed Jun. 23, 2015, and entitled, "Methods and Devices for Electrophoretic Sample Preparation." The present application incorporates herein by reference the disclosures of each of the above-referenced applications in their entireties.

GOVERNMENT LICENSE RIGHTS

This invention was made with government support under SBIR Phase II Grant No. 1R44HG008720-01 PI awarded by the National Institutes of Health. The government has certain rights in the invention.

FIELD OF THE INVENTION

Some embodiments of the present disclosure present apparatuses, methods and systems for isolating nucleic acid from a sample containing nucleic acid and other non-nucleic acid elements, as well as embodiments related to methods and devices for electrophoretic sample preparation.

BACKGROUND OF SOME EMBODIMENTS OF THE DISCLOSURE

Long-read sequencing and long-range mapping technologies may be used to generate more accurate genome assemblies. In short, there are many genomic regions, and many kinds of structural variation, that cannot be correctly assembled from short-read paired-end sequencing data, including typical sequencing data produced by the industry leaders (such as Illumina and Thermo Fisher Life Technologies). However, many of these regions and variations can be correctly assembled using newer technologies that generate primary read lengths (or genomic maps) measured in the 10's to 100's of kilobases (kb), such as those technologies developed by Pacific Biosciences, Oxford Nanopore, 10X Genomics, Genomic Vision, Roche/Genia, and Bionano Genomics.

Although the long-read technologies are still in an early stage of development, they may be used to complement short-read sequencing capabilities. For example, DNA extraction and library preparation technologies can be used to produce long and high-quality DNA libraries. However, a gap in the marketplace exists for commercial technologies that can produce long DNA fragments. Most commercial genomic DNA extraction kits yield maximum DNA size of 20-50 kb. Since some current systems are capable of primary reads greater than 50 kb, however, existing DNA extraction kits limit the capabilities of these systems. Additionally, long DNA fragments may be used for optical mapping and synthetic long-read systems (e.g., 10X Genomics, Bionano Genomics), which require libraries generated from genomic DNA samples that are 100's of kb in length. Therefore, there is a need for automated and reproducible methods for producing extremely long (e.g., 100's to 1000's of kb in length), high quality genomic DNA samples. Despite a demonstrated need and efforts to achieve these samples, a solution has not yet been developed.

In addition, library preparation is a multi-step process that is divided into two major divisions, 1) DNA extraction from biological samples (biological fluids, particulates, cells, and tissue), and 2) library construction. As DNA sequencing becomes more useful to clinical studies, diagnostics, and therapy management, integrated workflows may streamline and automate the overall process. Again, although there is a demonstrated need, increased integration of the overall sample to library workflow has not yet been achieved.

Furthermore, next-generation sequencing (NGS) for detecting and diagnosis of infectious disease has great potential in molecular diagnostics. For example, clinical workflows using clinical samples (frequently whole blood or white blood cells (WBC's) from whole blood) may be subjected to NGS sequencing, followed by in-silico subtraction of all sequences that can be mapped to the human reference sequence. The remaining "non-human" sequences are examined for identity with any known pathogen sequences. Although this process may be successful, it requires very efficient library construction methods and deep sequencing runs, both of which can be expensive. This expense has kept the in-silico subtraction method from widespread use.

SUMMARY OF SOME EMBODIMENTS OF THE DISCLOSURE

Embodiments of the present disclosure present a multitude of inventive concepts directed to, for example, apparatuses, systems and methods for isolating nucleic acid from a sample containing nucleic acid and other non-nucleic acid elements, as well as embodiments related to methods and devices for electrophoretic sample preparation. The following are illustrates of some of the embodiments disclosed herein.

A system for isolating nucleic acid from a sample may include a hydrogel matrix configured to immobilize a sample comprising nucleic acid and non-nucleic acid elements. The system may also have a reagent that is configured to diffuse into the hydrogel matrix, react with the immobilized biological sample, and release non-nucleic acid elements of a sample of cells. Additionally, the system may include means to elute the nucleic acid from the hydrogel matrix after the release of the non-nucleic acid elements.

In some embodiments, the hydrogel matrix may comprise agarose gels. The hydrogel matrix may contain approximately equal parts by volume of hydrogel and the biological sample. The reagent may be detergent solutions for lysis, solutions containing enzymes configured to digest bacterial, fungal, and/or plant cell walls, protease solutions, solutions containing DNA processing enzymes, solutions containing enzymes and synthetic adapters for creating sequencing libraries, and/or solutions containing transposasomes.

The system may also comprise at least one automated liquid handling device configured to do either or both of: mix the biological sample with molten gel containing hydrogel to prepare the hydrogel matrix, and regulate addition and removal of the reagent. The system may have a carrier configured with a shape to interdigitate with the hydrogel matrix, so as to allow attachment of the hydrogel matrix to the carrier. In some embodiments, the system may also have a filtration membrane that aids in the electrophoretical elution of the nucleic acid from the hydrogel matrix, and the filtration membrane may contain pores sized to selectively retain the nucleic acids based on size.

A method for isolating nucleic acid from a sample containing nucleic acid and non-nucleic acid elements may also be provided. The method may include mixing the sample with a molten hydrogel in a temperature regulated container, and the temperature of the container may be reduced in order to cause gelling of the mixture of the biological sample and the molten hydrogel to form a hydrogel matrix. The hydrogel matrix is configured to immobilize the biological sample. A reagent may be introduced to the hydrogel matrix, and the reagent may be configured to diffuse into the hydrogel matrix in order to react with the immobilized biological sample and release the non-nucleic acid elements. The nucleic acid may then be extracted from the hydrogel matrix.

In some embodiments, the hydrogel matrix may include agarose gel, and the biological sample may comprise DNA molecules. Additionally, an automated liquid handling device may be used to mix the biological sample with the molten hydrogel.

Furthermore, in order to introduce the hydrogel matrix to the reagent, a carrier carrying the hydrogel matrix may be dipped into a mixture of the reagent. The reagent may also be introduced to the hydrogel matrix by electrophoretically moving the reagent into the hydrogel matrix.

In some embodiments, the method may include filtering the nucleic acid using a filtration membrane containing pores sized to selectively retain the nucleic acids based on size. The method may also include removing non-nucleic acid elements from the hydrogel matrix electrophoretically following the release of the non-nucleic acid elements.

An electrophoresis cassette may include a container having an electrophoresis buffer, an electrophoresis gel matrix portion that is configured within the container, and a sample well configured within the electrophoresis gel matrix portion. The electrophoresis gel matrix portion may extend laterally across the container to divide the container into two chambers. Each of the portions may be filled with an electrophoresis buffer. The sample well may be isolated from the electrophoresis buffer by the electrophoresis gel matrix portion.

The electrophoresis gel matrix portion may be agarose, or it may be at least one of starch, agar, agarose, and polyacrylamide. The electrophoresis buffer may have a pH between pH 7 and pH 9, and it may comprise EDTA as a chelating agent.

In some embodiments, the cassette may also comprise at least one positive electrode and at least one negative electrode, with the positive electrode connected to a first of the chambers and the negative electrode connected to the second of the chambers. The chambers may be filled with electrophoresis buffer and may be configured to receive lysis reagents. A reagent well may be disposed between the sample well and the second of the two chambers. The lysis reagents may be one or more of anionic detergent and detergent-compatible protease. If the reagent includes anionic detergent, the detergent may be SDS with a concentration between about 0.1% and about 10% wt/vol. The lysis reagent may also be a mixture of anionic detergent SDS and proteinase K.

When a voltage is applied across the electrodes, the lysis reagent may be driven through the electrophoresis gel matrix portion and into the sample well. In some embodiments, the sample well contains a biological sample, applying the voltage causes DNA molecules within the biological sample to accumulate on a side of the sample well near the second of the two chambers. Reversing the voltage may move the DNA molecules away from the side of the sample well.

An electrophoresis system is also provided. The system may include an electrophoresis gel matrix that has a first end, a second end, a length, a width, a first lengthwise side and a second lengthwise side. A reagent well may contain a reagent and may be configured within the electrophoresis gel matrix portion proximate the first end. A sample well, which contains a sample of biological cells, may be configured within the electrophoresis gel matrix proximate the first end and between the reagent well and the second end. A first negative electrode of a pair of electrophoretic electrodes may be arranged at the first end, and a first positive electrode of the pair of electrophoretic electrodes may be arranged at the second end. Application of a first biasing voltage across the pair of electrophoretic electrodes may cause the reagent to be driven from the reagent well into and/or through the sample well.

In some embodiments, the sample well may include a cell suspension, and the reagent well may include a negatively charged lysis reagent. As a result of lysis from the lysing agent, DNA molecules of the cells contained in the cell suspension may be produced. The DNA molecules may accumulate on at least one side of the sample well, and, upon application of a second biasing voltage across the pair of electrophoretic electrodes, the accumulated DNA may electrophorese out of the sample well.

The system may also comprise a plurality of elution receiving areas or channels that are arranged along the first lengthwise side of the gel. Each receiving area may have a first side arranged adjacent the first lengthwise side of the gel and second side spaced apart from the first side of the receiving area. Further, the system may include a plurality of pairs of elution electrodes where each pair corresponds to an elution receiving channel. A first negative elution electrode of a first pair of elution electrodes is arranged proximate the second lengthwise side of the gel across from the first side of a first elution receiving channel, and a first positive elution electrode of the first pair is arranged proximate to the second side of the first elution receiving channel. The second activation may cause DNA fragments of the electrophoresed DNA to accumulate proximate one and/or another of the elution receiving channels. Furthermore, application of a biasing voltage across one and/or another of the pairs of elution electrodes drives the DNA fragments into one and/or another of respective elution channels.

A method for electrophoresis may include the electrophoresis system described above. A sample may be loaded into the sample well, and a reagent may be loaded into the reagent well. A first voltage bias may be applied across the pair of electrophoretic electrodes which is configured to cause the reagent to move from the reagent well to the sample well. The reagent may be configured to cause the cells in the suspension to lyse, and DNA molecules form the cells accumulate on at least one side of the sample well.

In some embodiments, DNA fragments may be electrophoretically driven from the sample well to the plurality of elution channels. The method may further comprise incubating the cell suspension within the sample well and/or breaking down the DNA molecules into fragments. Additionally, the incubation of the cell suspension may include successively adding and incubating a first, second, and/or third additive to the sample well and incubating with the contents of the sample well the cells therein. The first, second, and third additives may also be added simultaneously. In some embodiments, the first additive is Tn and PacBio adapters, the second additive is T4pol, dNTPs, *E. coli* ligase, and NAD, and the third additive is Exonuclease T5.

It will be appreciated by those of skill in the art that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

FIGS. 15A-C show top view of cassettes according to some embodiments.

FIGS. 16A-L show an exemplary workflow using a cassette according to some embodiments.

Figure 1:
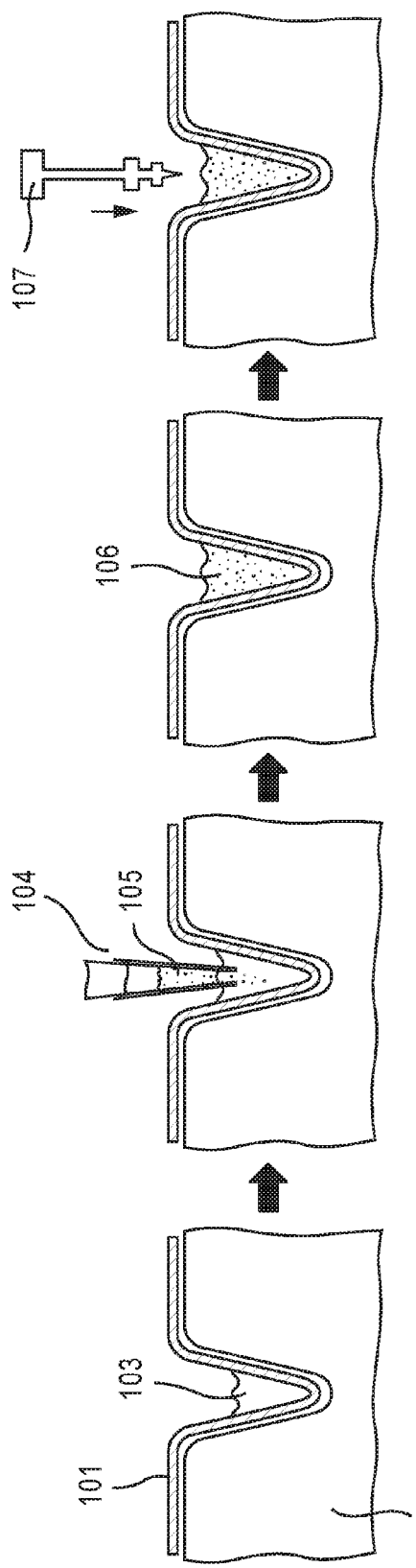
FIG. 1 shows a cross-sectional view of hydrogels, such as but not limited to agarose gels, which may be used to prepare high molecular weight (HMW) nucleic acids, e.g., DNA, according to some embodiments.

One of ordinary skill in the art will understand and appreciate that the drawings of the subject disclosure are primarily for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF SOME OF THE EMBODIMENTS

In some embodiments, hydrogels can be used in some of the processes of preparing HMW nucleic acids. In some embodiments, hydrogel supports (e.g., agarose gels) are utilized for automated extraction and processing of HMW nucleic acids. The gels may be formed on solid supports of various kinds that simplify handling and enable automated processing of the gel-embedded samples. Examples of particulate biological samples comprise animal, plant, fungal, or bacterial cells. Further, in some embodiments, the particulate samples comprise non-living biological particles, including viruses, and non-cellular membrane-delimited vesicles containing nucleic acids.

In some embodiments, the particulate biological sample is embedded in a hydrogel matrix for subsequent processing. Examples of hydrogel matrices are those that are useful for biomedical applications, such as those discussed in Hoffman, Allan S. *Advanced Drug Discovery Reviews*, Vol. 54, pp. 3-12, 2002, and food and microbiological applications, such as those discussed in *Food Polysaccharides and their Applications*, Ed. By A. M. Stephenson and G. O. Philips, 2006. The entire contents of these publications, and the references cited therein, are expressly incorporated by reference herein. In some embodiments, hydrogel matrix is agarose. Although much of the discussion in the instant description deals with hydrogel supports comprising agarose, the use of agarose in the following description should be considered exemplary and non-limiting.

In some embodiments, the hydrogel matrix may have substituent groups that can be selectively bound by one or more of the sample constituents. Such interactions may cause selective retention of one or more sample constituents during processing of the sample, or during elution of the processed nucleic acids.

In some embodiments, with reference to FIGS. 1A-H, the use of hydrogels such as, but not limited to, agarose gels in preparing high molecular weight (HMW) nucleic acids, e.g., DNA, is disclosed. For example, a container 101 is placed in contact with a thermally regulated support 102, such as, but not limited to, a programmable thermocycler. A volume of molten agarose gel in an appropriate buffer may then be placed in the container and maintained at a temperature sufficient to keep the molten mixture from gelling. In some embodiments, a low melting temperature agarose may be used to limit exposure of the sample to heat during gel formation (for example, for SeaPlaque® agarose from the company Lonza, the melting temp of 1.5% gel is approximately 65° C., and the gelling temperature is approximately 30° C.). In some embodiments, when using hydrogels that may be pH-sensitive, acidic systems may be used to regulate the gelling properties of the hydrogel. In some embodiments, hydrogels may be light sensitive, and light (e.g., ultraviolet radiation, visible light, etc.) may be used to regulate the gelling properties of the hydrogel. While the gel is incubated above its gelling temperature, a fluid liquid sample 105 comprising the biological material sample of interest may be mixed with the molten gel solution. In some instances, the biological sample is added manually and/or via automated liquid handling devices, e.g., 104. In some embodiments, the volumes of gel solution and/or biological sample are selectively chosen so that the final gel sample includes a sufficiently high agarose concentration to be easily manipulated in subsequent steps. For example, for a molten gel solution at about 1.5% agarose, the volumes of molten gel solution and biological sample may be approximately equal so that the final gel solution 106 has a gel concentration of at least 0.75%.

The final mixture comprising gel and biological sample may be maintained just above the gelling temperature in the container 101, and a carrier 107 may be immersed in the molten mixture. After the carrier is immersed in the molten mixture, the temperature of the support 102 is reduced to a temperature below the gelling temperature, allowing the mixture comprising gel and biological sample to solidify (e.g., on the carrier). In some embodiments, the carrier may be an injection molded plastic part, and may have a shape that is designed to interdigitate with the gelled sample plug 108. For example, the carrier may provide fins or projections for good mechanical support for the gel, and thereby allow the sample plug to remain attached to the carrier. In some embodiments, the sample plug 108 may be removed from the original container 101 using the upper portion of the carrier as a handle for manual manipulation, or alternatively, using the upper portion of the carrier as an attachment point for automated robotic handling of the sample plug.

In some embodiments, the sample plug may be immersed in a reagent mixture 110 in a second container 109. Further, the carrier 107, and/or second container 109 may be agitated, to facilitate mixing between the reagent mixture 110 and the sample plug 108. In some embodiments, the sample plug formed on the solid carrier may be very thin, preferably less than 1 millimeter in thickness (e.g., 0.5 mm, 0.4 mm, 0.3 mm, 0.2 mm, 0.1 m, 0.05 mm, 0.01 mm), to facilitate diffusion of processing reagents into the gel support. In some embodiments, the thickness of the gel layer is less than 200 micrometers. Supports with sub-millimeter thickness are useful for allowing diffusion of enzymatic processing reagents, such as proteases, in and out of the gel support.

In some embodiments, addition of processing reagents to the sample plug may be accomplished by remelting the sample plug in a container holding a reagent, mixing the molten gel and reagent to disperse the reagent throughout the mixture comprising the gel and the biological sample, and regelling the mixture. In such embodiments, the reagent may be added to the container in liquid form, or may be added in gel-embedded form. If the reagent is added in liquid form, the reagent addition may not dilute the mixture so that subsequent gelation is prevented, or so that the sample plug becomes fragile. If reagent is added in gel-embedded form, the gel used may melt and re-gel under the same conditions used for the sample plug. In embodiments where the addition of processing reagents are added by remelting the sample plug, hydrogel matrices which can be melted or liquefied at low temperature may be used. For example, the matrices may be low melting temperature agarose (such as SeaPlaque® agarose from Lonza). In embodiments where addition of processing reagents is performed by remelting the sample plug, the mixing step may be done as gently as possible to avoid shear damage to the nucleic acids.

Figure 2:
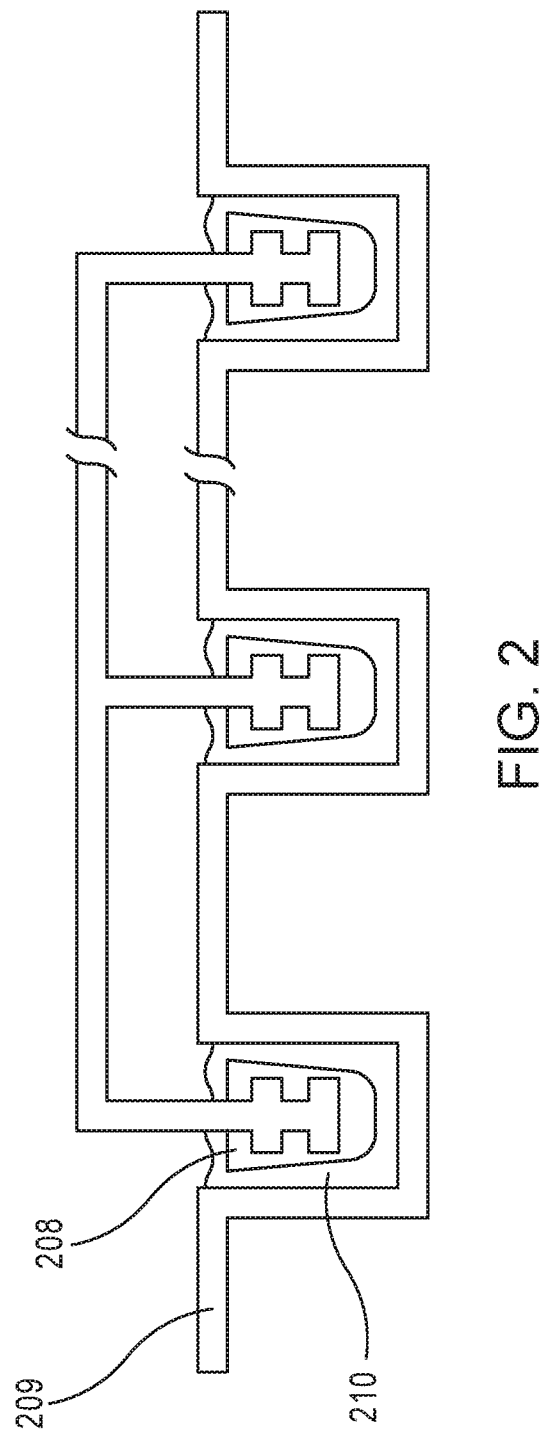
FIG. 2 shows an example configuration of the system described herein to process a plurality of biological samples in parallel according to some embodiments.

In some embodiments, with reference to FIG. 2, the system may be configured to process a plurality of biological samples in parallel. For example, the carrier may have a comb shape, capable of carrying a plurality sample plugs 208, and processing those plugs in multi-well containers 209 each carrying an aliquot of reagent 210.

Figure 3A:
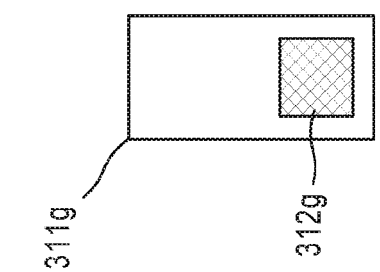
FIG. 3 shows examples of porous elements included in the carrier to facilitate attachment of the sample plug to the carrier according to some embodiments.
Figure 3C:
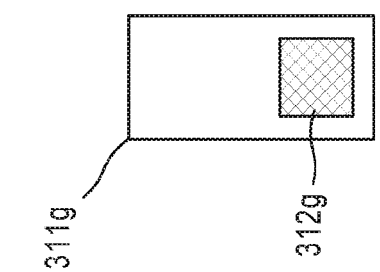
Figure 3E:
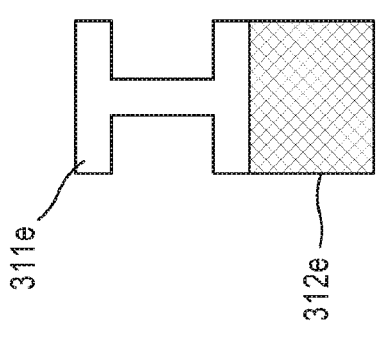
Figure 3G:
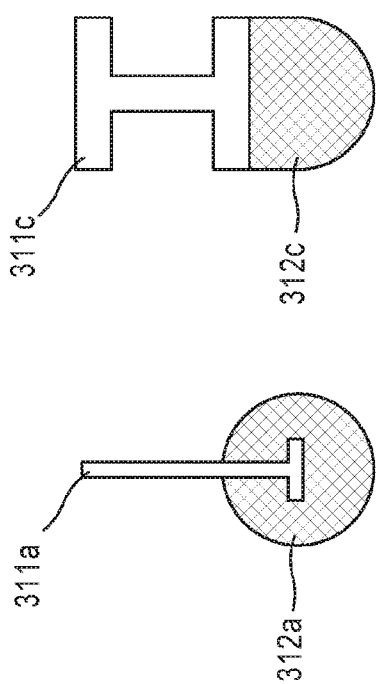
Figure 3B:
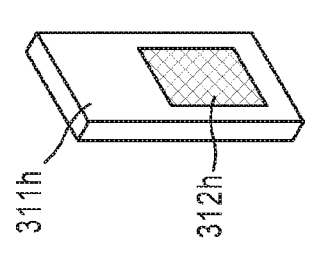
Figure 3D:
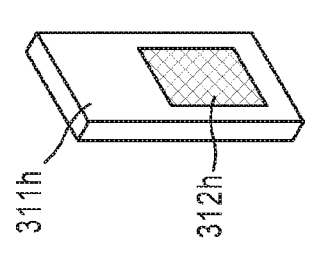
Figure 3F:
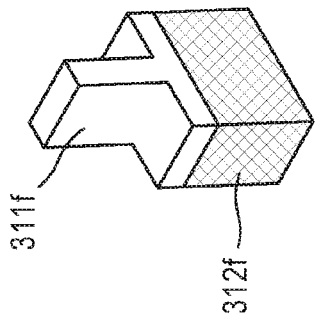
Figure 3H:
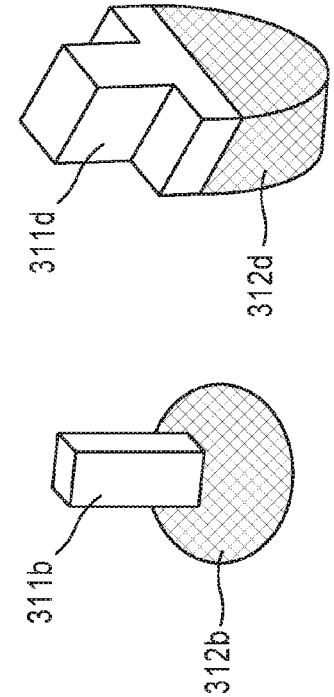

With reference to FIGS. 3A-H, in some embodiments, the carrier may comprise a porous element 302 to facilitate attachment of the sample plug to the carrier. In some embodiments, the porous element is attached to a solid portion 311 to facilitate manipulation of the carrier. Exemplary materials for the solid portion include, but are not limited to, injection moldable plastics. Exemplary materials for the porous element include, but are not limited to, papers, filters, plastic or glass wool, porous sintered glass or plastic, woven materials such as plastic mesh or fabrics. The porous element of the carrier may be have a variety of shapes, non-limiting examples of which are shown in FIG. 3, including round (FIGS. 3A and 3B), semi-circular disk (FIGS. 3C and 3D), rectangular (FIGS. 3E and 3F), and rectangular with a solid border (FIGS. 3G and 3H).

Figure 4:
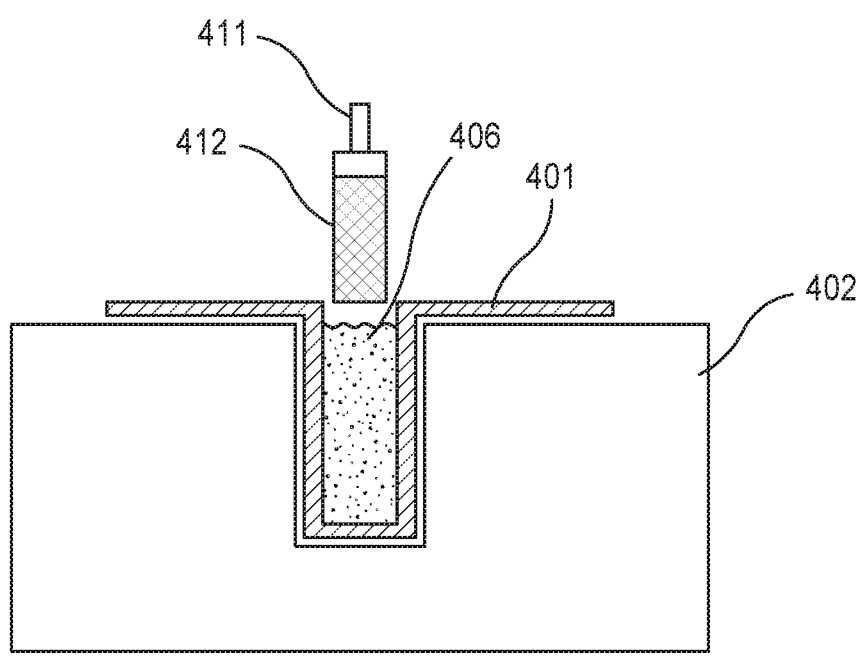
FIG. 4 shows an aspect of the formation of the sample plug with a carrier comprising a porous element according to some embodiments.
Figure 5A:
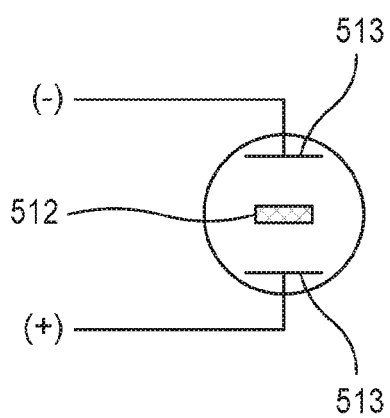
FIGS. 5 and 6 show an illustration of electrophoresis which may be used to accelerate the processing of gel plugs according to some embodiments.
Figure 5B:
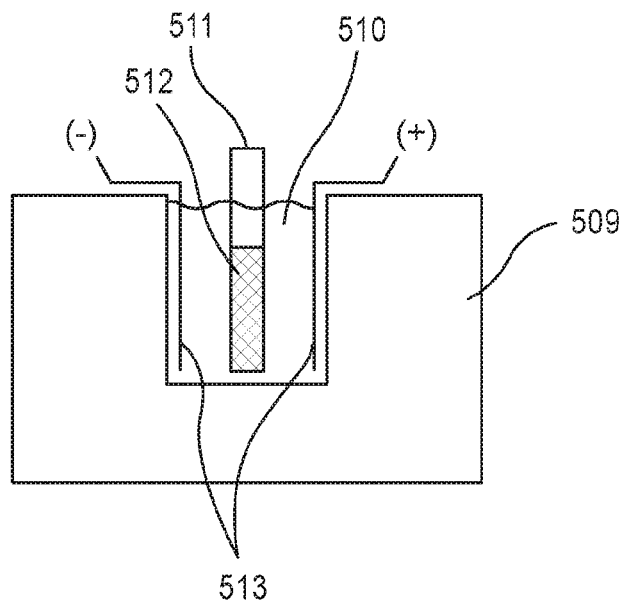
Figure 5C:
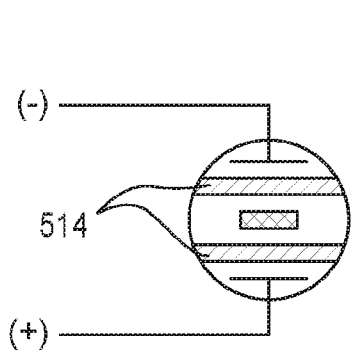
Figure 5D:
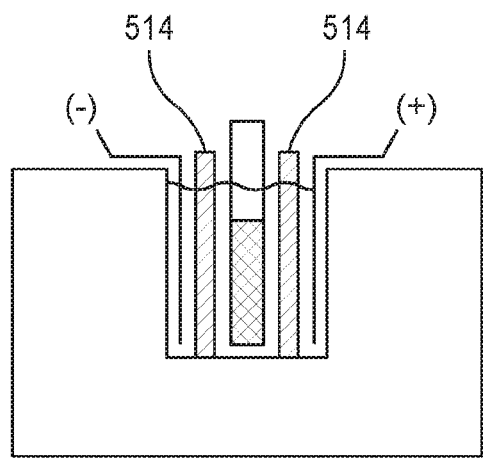

With reference to FIG. 4, in some embodiments, the formation of the sample plug with a carrier comprising a porous element is illustrated. The molten mixture comprising gel and biological sample is held above the gelling temperature in a container 401 held in a thermally regulated support 402. The carrier is immersed into the liquid mixture so that the liquid mixture fills the porous element of the carrier. In some embodiments, the mixture fills the porous element evenly without inclusion of airspaces/or bubbles inside the porous element. After immersion of the porous element into the molten mixture comprising gel and biological sample, the temperature of the thermally regulated support is lowered to allow gelation of the sample plug. In some embodiments, the cavity of the container 401 holding the mixture can be approximately the same dimensions as the porous element of the carrier, so that there is little or no unsupported sample plug outside of the porous element of the carrier.

In some embodiments, the system described herein may be used to perform sequential chemical and/or enzymatic processes on a sample plug, as shown, for example, in FIGS. 1G and 1H. The carrier with sample plug can be incubated sequentially in a plurality of containers 109 each with a different reagent 110. Non-limiting examples of reagents useful for DNA extraction and processing include: detergent solutions for lysis; solutions containing enzymes for digesting bacterial, fungal, or plant cell walls; protease solutions; solutions containing DNA processing enzymes; solutions containing enzymes and synthetic adapters for creating sequencing libraries; and solutions containing transposasomes for constructing sequencing libraries. In such embodiments, it may be useful to include one or more incubations in reagent containers containing with solutions of pure buffers, to allow reactants from a previous step to diffuse from the sample plug, leaving behind the modified DNA products. In some embodiments, a biological sample in a hydrogel may be processed to as to fractionate the sample into subcellular compartments, e.g. treatment of whole blood or dispersed mammalian cells with a solution containing a detergent such as Triton X 100, at 0.1-1%, wt/v, will lyse mammalian plasma membranes, but leave nuclei intact.

In some embodiments, the system may be configured so that a series of reagents are serially added and removed from a single reagent container 109. The addition and removal of the reagents may be accomplished via fluidic channels within the container, said channels connecting to a one or more liquid handling means (e.g., reagent container) external to the container. In other embodiments, the reagents may be added and removed from the top of the container by standard liquid handling means (such as, for instance, a gantry-style liquid handling robots sold by Beckman, Agilent, Tecan, Hamilton, etc.). In both such embodiments, the carrier with sample plug could remain resident inside, or close to, the reagent container during reagent exchange.

In some embodiments, the sample plug may be formed with a higher concentration of agarose to facilitate processing workflows that generate smaller DNA fragments. A non-limiting example of such a workflow would be transposase-mediated generation construction of short-read next-generation libraries (e.g., using Nextera from Ilumina®, MuSeek from Thermo Fermentas, etc., chemistries). In some such workflows, DNA is fragmented into sizes ranging from several hundred to several thousand bp in length. In such workflows, a higher concentration of agarose in the sample plug will restrict diffusion of the library products from the plug, but would still allow the transposase and free adaptors to be removed efficiently.

With reference to FIGS. 5A-D and 6A-B, in some embodiments, electrophoresis may be used to accelerate processing of gel plugs. Gel plugs having a relatively thin planar form, such as those shown in FIGS. 3C-3H, may be used allowing the various components of the sample plug (including sample DNA, non-DNA sample components, and reagents) to respond to imposed electric fields uniformly and rapidly. In employing electrophoresis, for example, the reagent container 509, 609 may be fitted with a pair of electrodes 513, 613 on opposite sides of the container 509, 609. The sample plug 512, 612 may be immersed into the reagent 510, 610 within the container between the two electrodes, and a voltage is placed across the electrodes such that sample components inside the plug can be moved out of the plug, or components of the reagent solution can be moved into the plug. In some embodiments of the electrophoretic method, it may be useful to use conductive barriers 514, 614 to prevent electrolysis products from reaching the DNA in the sample plug 512, 612. Examples of such barriers are described in U.S. Pat. No. 5,929,208, U.S. Pat. No. 6,306,348, and U.S. Pat. No. 6,319,472. The entire contents of these patents, and references cited therein, are expressly incorporated by reference herein.

When performing a series of reagent exchanges into and out of the sample plug, gel concentration, voltage, and/or electrophoresis duration may be chosen so that the reagent components are efficiently exchanged, and/or so that the DNA is remains in the sample plug. Since HMW DNA migrates so slowly in agarose, usually, such conditions are fulfilled for very HMW DNA. Higher concentration gels, lower voltages, and more optimization may be used when generating short read libraries (e.g., about 500 bp fragment size).

Figure 6B:
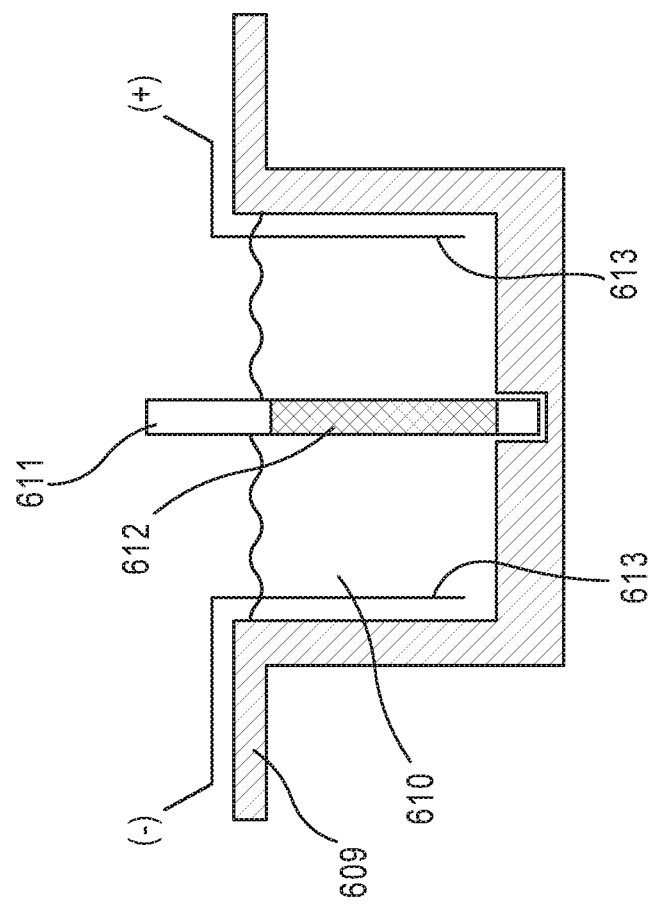
Figure 6A:
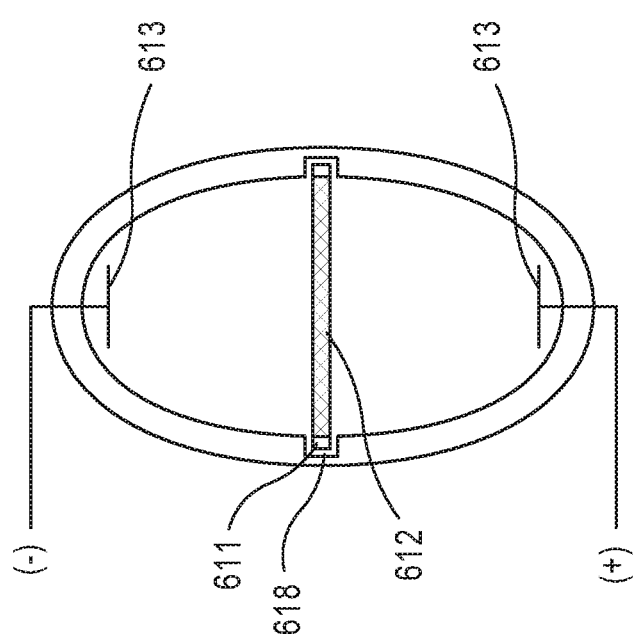

FIGS. 6A-B show electrophoresis with carriers in the form shown in FIGS. 3G and 3H. In some embodiments, the gel plug is supported on a porous element that is attached to the carrier on all edges. Therefore, the finished sample plug forms a window through the carrier. The carrier is inserted into the reagent container 609 in a manner that divides the reagent container into two chambers, each containing its own electrode 613. In some instances, the carrier and/or sample plug may provide a liquid-tight seal between the two chambers. Allowing for keeping the carrier within a single container 609 and carry out serial processing steps on the sample plug by exchanging the reagent 610 on one or both sides of the carrier. Electrophoresis can be used to drive new reagent into the sample plug, and remove old reagent from the sample plug.

Figure 7A:
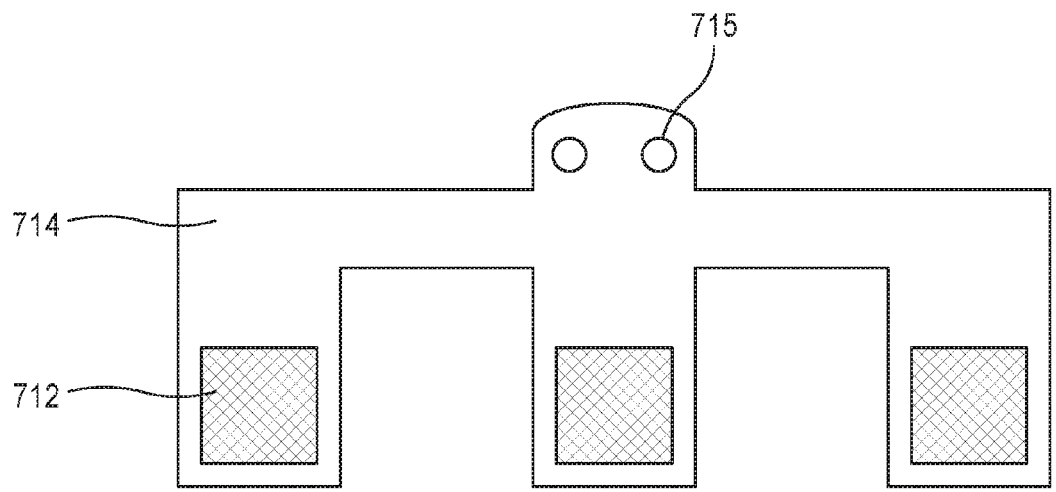
FIG. 7 shows a multiplex embodiment of the configuration shown in FIG. 6.
Figure 7B:
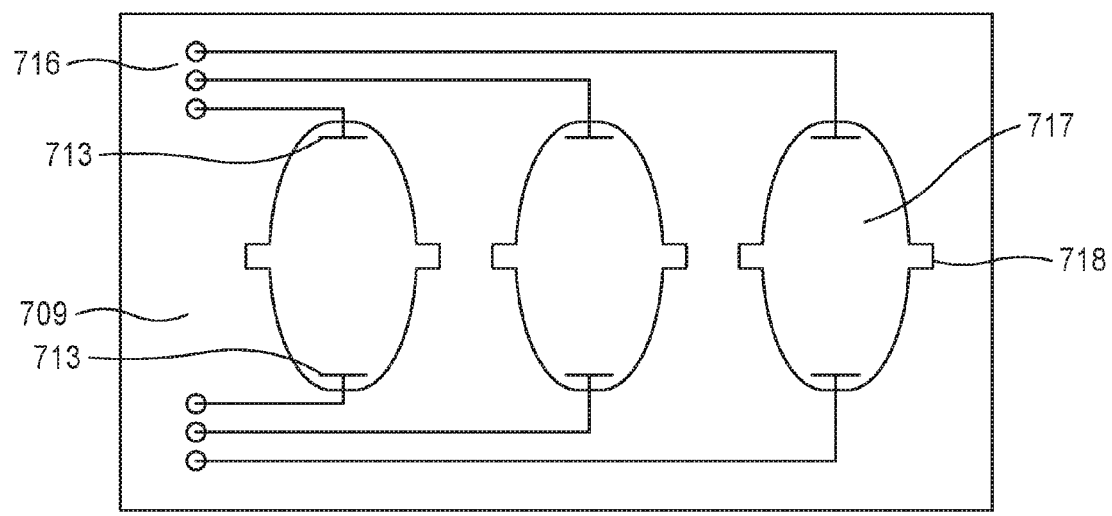

With reference to FIGS. 7A-B, in some embodiments, a multiplex of the inventive concept shown in FIGS. 6A-B is illustrated. FIG. 7A shows a multiplex carrier 714 having a comb-like shape. Each tooth forms a carrier for a sample plug 712, similar to the single sample carrier shown in FIGS. 3G and 3H. The comb has a region 715 for attachment to automated movement means by which the comb may be automatically and/or robotically inserted into, and/or removed from, reagent containers in automated processing workflows. In FIG. 7B, a multiplex reagent container 709 for processing the comb-like carrier of FIG. 7A is shown. The container is designed to receive the comb at a specific position 718 within the container. In the embodiment of FIG. 7B, the comb is designed to be inserted into a set of slots 718 in each cavity of the container. A set of electrodes is provided in each cavity of the container. In this non-limiting example, each electrode can be separately addressed through contacts 716 at the left edge of the container. The embodiments of FIGS. 7A-B are exemplary, and many other electrode and comb placement arrangements may also compatible with one and/or another of the embodiments disclosed herein.

In some embodiments, processed nucleic acid, such as but not limited to DNA, may be eluted from the sample plug by electrophoresis. In some instances, a device of the general design shown in FIGS. 5C and 5D may be used for electroelution of the processed nucleic, where the barrier 514 nearest to the positive (+) electrode comprises an ultrafiltration membrane of a pore-size small enough to retain the processed nucleic acids. One such exemplary membrane is a polyethersulfone membrane with a 10 kDa molecular weight cutoff (Biomax® 10 kDa from EMD Millipore).

In some embodiments, the electric field used for electroelution may be manipulated to selectively recover certain size ranges of processed nucleic acids. For instance, pulsed field methods may be used to elute processed DNA fragments 50-500 kb in length while leaving DNA fragments greater than about 2000 kb in size in the sample plug, as has been shown by Jann Noolandi, and Chantal Turmel in *In Methods in Molecular Biology Volume* 12: *Pulsed-field gel electrophoresis, Protocols, Methods, and Theories. Ed.* Burmeister, Margit, and Ulanovsky, Levy. Humana., pp. 73-103 and 135-143, which is hereby incorporated by reference in its entirety. If the larger size fraction is desired free of the lower, the lower fraction can be eluted first under size-selective pulsed field conditions, and subsequently the higher fraction can be recovered under other pulsed field conditions or under continuous field conditions. In such embodiments, the carrier may be moved to a second elution container (e.g., FIGS. 5C and 5D) for the second elution in order to avoid carry-over contamination from the unwanted first elution products.

In some embodiments, the carrier containing the processed sample plug may be used to load the processed nucleic acids into other electrophoretic devices for analysis or for other sample preparation processes, such as, for example, size selection. For example, the multiplex carrier concept shown in FIG. 7A could be used to load analytical agarose slab gels, so that the teeth of the comb fit into the sample loading wells of the analytical slab gel. In a similar manner, such comb designs could be used to load preparative electrophoretic size selection systems such as those described in U.S. Pat. Nos. 8,361,298 and 8,361,299, both of which are hereby incorporated by reference in their entireties. Additional sample preparation methods and devices are explained after the exemplary experimental implementations Exemplary Experimental Implementations
According to Some Embodiments Example: Preparation of Very High Molecular Weight DNA from Bovine Whole Blood Using an Agarose Sample Plug with Rapid Electrophoretic Purification Immobilization of Blood Cells in Agarose.
Prepare 2% agarose (SeaKem Gold, Lonza) by adding 2 g agarose to 100 mL of 1×KBB/2 mM EDTA (50 mL 10×KBB, 2 mL 500 mM EDTA to 500 mL).
Cool an aliquot to 45 C.
Mix 2 mL of agarose with 2 mL of whole bovine blood (Lampire Biologicals), and pour into a 60 mm diameter petri dish; allow to cool.
(0.5×KBB buffer is 51 mM Tris base, 28.8 mM TAPS acid, 0.08 mM EDTA acid, pH 8.7.)
Electrophoretic Deproteinization
Trial 1: Deproteinization from SDS Buffer.
  Prepare a horizontal agarose gel in a Galileo galileo 1214 gel box tray with two 12 well 1.5 mm thick combs, add 100 mL of 1% SeaKem Gold agarose (Lonza) in 0.5×KBB+0.5% SDS.
  From the petri plate with whole blood/agarose, punch out 6.35 mm diameter discs, and transfer to the wells of the agarose gel.
  Deproteinize by electrophoresis at 250V 21 min.
  Remove discs from wells, and transfer to a fresh petri dish with TE.
Trial 2: Deproteinization from SDS/Thiourea Buffer
  All steps performed as in Trial 1 above, except that the gel contains 2M thiourea in addition to components listed above; this gel requires cooling (4 C, 30 minutes) to set.
Restriction Enzyme Digestion
Discs are in petri dishes in TE
Remove a disc from TE with plastic spatula, blot dry by tapping an edge against a paper towel, and add to a 2 mL microfuge tube with
78 uL water/16 uL 10×NEB buffer/1 uL 1M DTT/3 uL NEB BSA and enzyme as follows.

| Trial | Disc | Buffer | Enzyme |
|---|---|---|---|
| 1 | 0 | custmart | none |
| 1 | 1 | cutsmart | XhoI |
| 1 | 2 | cutsmart | ApaI |
| 1 | 3 | cutsmart | HinfI |
| 1 | 4 | cutsmart | DraI |
| 1 | 5 | 1.1 | KpnI |
| 1 | 6 | 2 | HinDIII |
| 1 | 7 | 3.1 | PuvI |
| 1 | 8 | R1 | EcoR! |
| 2 | 9 | cutsmart | XhoI |
| 2 | 10 | cutsmart | HinfI |
| 2 | 11 | cutsmart | DraI |

Figure 8A:
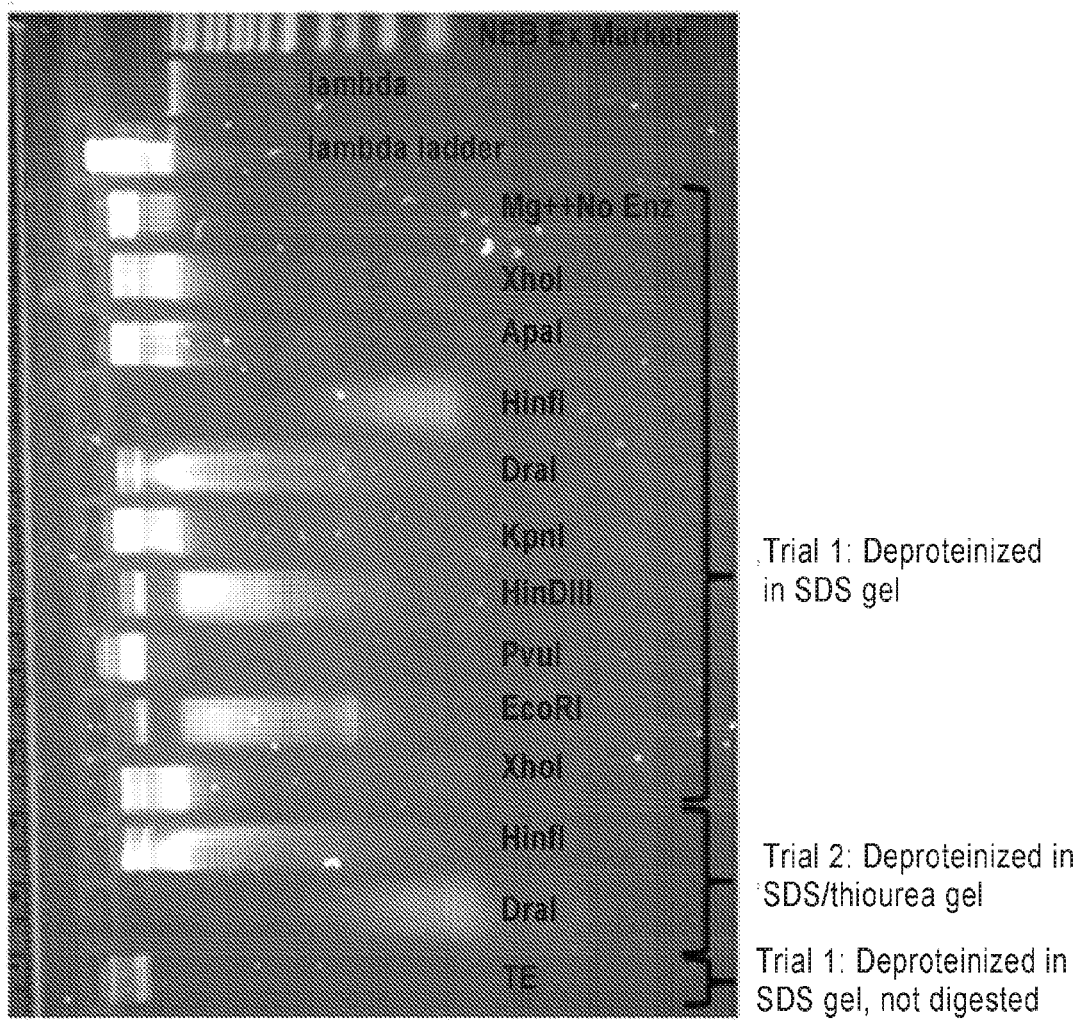
FIGS. 8A and 8B show examples of gel samples loaded on analytical gel according to some embodiments.
Figure 8B:
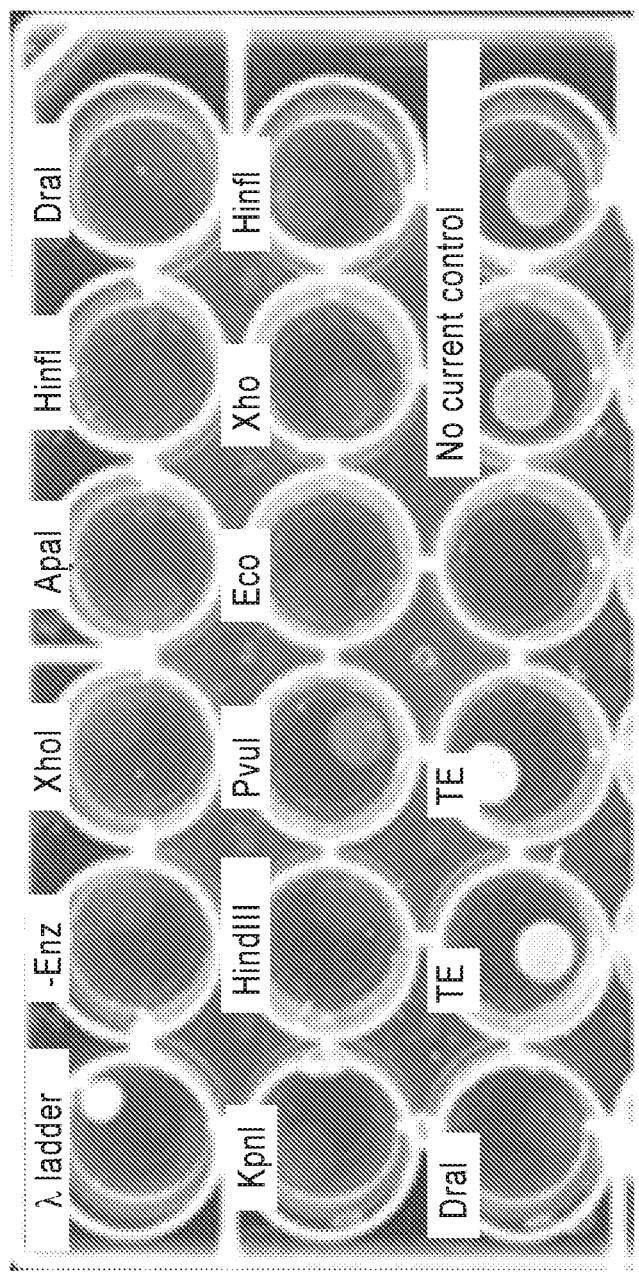

All Enzymes are from NEB and (except EcoRI and Apa) at 10 or 20 u/uL. All digests used 2 uL enzyme/well, except for EcoRI (100 u/uL) and ApaI 50 u/uL), in which cases onlyluL of enzyme. All were incubated at 37 C overnight. Reactions were terminated with 8 uL of 0.5M EDTA (~25 mM) and 8 uL of 10% SDS (~0.5%)
The reactions using Cutsmart have a strong ppt, probably due to the K+ in the buffer.
Analytical Agarose Gel Electrophoresis
Prepare a horizontal gel with 1% seakem gold and 0.5×KBB buffer; transfer discs from above to sample wells; run using the Pippin Pulse (Sage Science), at 80V, with field parameters (constants A-G) as 300, 100, 30, 10, 30, 10, 45 (MJ5 protocol) for 12 hours.
Standards include a low molecular weight marker (NEB extend ladder), lambda genomic DNA (48.5 Kbp) and NEB lambda ladder PF standard.
Description of Gel Samples Loaded on Analytical Gel (FIGS. 8A-B)

| PF gel lane | Mol Wt Std | Deprot Trial | Disc # NEB Buffer Enzyme | Enzyme site Comment (CpG sites) |
|---|---|---|---|---|
| 1 | NEB extend Ladder | | | |
| 2 | Lambda DNA | | | |
| 3 | Lambda Ladder | | | |
| 4 | | 1 | 0, cutsmart, none | — |
| 5 | | 1 | 1, cutsmart, XhoI | CTCGAG One CpG site |
| 6 | | 1 | 2, cutsmart, ApaI | GGGCCC Two potential CpG sites |
| 7 | | 1 | 3, cutsmart, HinfI | GANTC Two potential |
| 8 | | 1 | 4, cutsmart, DraI | TTTAAA |
| 9 | | 1 | 5, 1.1, KpnI | GGTACC Two potential |
| 10 | | 1 | 6, 2, HindIII | AAGCTT |
| 11 | | 1 | 7, 3.1, PvuI | CGATCG Two; enzyme predicted to give avg size >200 Kb on mammalian DNA |
| 12 | | 1 | 8, EcoRI, EcoRI | GAATTC Two; Bovine Genome has a 1,400 bp repeat when cut with EcoRI |
| 13 | | 2 | 9, cutsmart, XhoI | |
| 14 | | 2 | 10, 2, HindIII | |
| 15 | | 2 | 11, cutsmart, DraI | |
| 16 | | 1 | Disc Left in TE overnight | |

Staining of Sample Plugs after Analytical Gel Electrophoresis
After analytical gel electrophoresis, the sample plug discs were removed from the gel loading wells, and stained in 700 uL 0.5 ug/mL ethidium bromide in a 24 well microplate. Control discs which had been deproteinized, but had not been run on the analytical gel were also stained and are shown in the lower right wells.
Gel was stained with ethidium bromide and photographed with a UV transillumination, and images were analyzed with CaptureNX software (Nikon).
Results:
The sample plugs that were electrophoretically deproteinized but remained in TE buffer without restriction enzyme treatment remained brightly stained by ethidium after analytical gel electrophoresis (FIG. 8B, bottom row, wells 2 and 3 from left). Very little DNA was electrophoresed from the undigested TE plug and migrated with an apparent size of ~100-150 kb (FIG. 8A, bottom lane). From the lambda ladder in the top lane of the analytical gel, it can be seen that lambda multimers of about 250 kb would enter the gel under the pulse conditions used. Therefore, DNA in the TE plug behaves as if it is substantially larger than 250 kb since under these pulse conditions it will not leave the gel.

All other restriction enzyme treatments, liberated large amounts of DNA from the sample plugs as seen from the stained plugs. There was some trace nuclease activity left over from the samples as seen in the plug treated with restriction buffer but no enzyme (FIG. 8A "Mg++No enz" lane, FIG. 8B, top row, $2^{nd}$ from left), but the activity was low enough so that most of the DNA migrating into the plug migrated with an apparent size greater than 150 kb. The size of the DNA liberated from the plugs correlated with the expected frequency of the enzyme cleavage sizes. In particular, bovine DNA has an abundant DNA repeat element that gives rise to a 1.4 kb on digestion with EcoRI, and this expected band is clearly seen in FIG. 8A. Taken together, these results suggest that most of the DNA in the deproteinized plugs is very high molecular weight linear double-stranded DNA.

Example: Rapid Removal of Protein from Agarose-Embedded Whole Blood Samples by Electrophoresis Goal:

Demonstrate that when whole blood is mixed with agarose, that all of the protein can be removed by electrophoresis in the presence of SDS, and compare the resulting protein profile of agarose plug samples to the protein profile of agarose plugs treated with Proteinase K.

Experimental

Mix Whole Blood with Agarose
To 2 mL of 1.5% seakem gold agarose, in 0.5×KBB buffer (Sage Science) plus 1 mM EDTA, at 48° C., add 2 mL of whole blood, and after rapid swirling to mix, pour the mixture into a 60 mm diameter petri dish and allow to cool.
Deproteinize by Treating with Proteinase K
Run 1: From the petri dish, use a punch to make a 6.35 mm diameter disc; incubate the disc overnight, with rocking, in a 2 mL microfuge tube with 1 mL of SarE buffer.
(SarE buffer: To make 1 mL, mix 375 uL water, 100 uL 10% wt/v N lauryl sarcosine, 500 uL Na2EDTA, and 25 uL of 20 mg/mL proteinase K solution (Fisher Scientific, catalog # FP2500150))
Run 2: Incubate a 6.35 mm disc as above, but with 1 mL of STCP buffer
STCP buffer: To make 1 mL, mix 890 uL water, 50 uL 10% wt/v SDS, 50 uL 1M Tris HCl, pH 7.5; 1 uL 1M CaCl2; 5 uL 20 mg/mL Proteinase K
Run 3: (no protease control): Incubate a disc as above, but with a buffer containing 0.5×KBB/0.5% SDS
Deproteinize by Electrophoresis in the Presence of SDS
Run 4: transfer a 6.35 mm disc to the well of an agarose gel (1% seakem gold, 0.5×KBB, 0.5% SDS, 1 mM EDTA). The running buffer is the same (0.5×KBB/0.5% SDS/1 mM EDTA). Gels (50 mL total volume of agarose) are poured in a Galileo bioscience model 0708 gel box, with a 1.5 mm thick comb with 6 well formers.

Electrophorese at 220V for 5 minutes; this time is sufficient for the dark brown hemoglobin band to completely clear the agarose disc.
Transfer the disc to a 2 mL microfuge tube with 1 mL of fresh running buffer.
Run 5: As run 4, but electrophorese for 8 minutes at 220V.
Run 6: As run 4, but after 4 minutes, fill the agarose gel well (containing the now colorless disc) with 5 mM TCEP solution; wait 5 minutes; electrophorese for 4 min at 220V.
Run 7: As run 6, but electrophorese for 8 minutes after TCEP addition.
Run 8: Control (no treatment) A 6.35 mm disc (bright red from the whole blood) without further treatment.
Determine the Extent of Deproteinization by Solubilizing Agarose Discs, and Running Soluble Material on Analytical SDS PAGE
Discs from runs were solubilixed by mixing with 80 uL of TUS buffer, 10 uL of 4×LDS sample buffer for SDS PAGE (invitrogen) and 1 uL of 500 mM TCEP solution, and heating for 85° C. for 6 minutes.
(TUS buffer is made by combining 3 gr thiourea; 260 uL 50×TE (USB biochemicals); 2.6 mL 10% SDS; and water to 13 mL; this solution is soluble at 42° C. This buffer is approximately 3M in thiourea, 1×TE and 2% in SDS.)
20 uL of the solubilized material was loaded on a 4-20% gradient SDS gel (Genscript, ExpressPlus PAGE Gel, 4-20%, 15 wells; Catalog No: M42015).
Controls for Gel Analysis
A: 5 uL whole blood+80 uL TUS, 10 uL 4×LDS, 1 uL TCEP
B: 1 uL whole blood+80 uL TUS, 10 uL 4×LDS, 1 uL TCEP
C: 2 uL 20 mg/mL proteinase K++80 uL TUS, 10 uL 4×LDS, 1 uL TCEP
The gel was run in at 19 watts constant power until the tracking dye reached the bottom; the gel was rinsed with water and stained with Coomassie Blue (Thermo fisher catalog #24620, PageBlue Protein Staining Solution), destained with water, and photographed using a lightbox (transllumination). Images were analyzed with Capture NX software (Nikon).
Loading of samples in FIGS. 9A and 9B.

| Lane | Sample, 20 uL of TUS solubilized protein/agarose, except as noted |
|---|---|
| 1 | None |
| 2 | 10 uL of Lonza catalog # 193837 quadcolor protein marker |
| 3 | Run 1, disc incubated with SarE buffer |
| 4 | Run 2, disc incubated with STCP buffer |
| 5 | Run 4, disc deproteinized 4 min @220 V |
| 6 | Run 5, disc deproteinized 8 min @220 V |
| 7 | Run 6, disc deproteinized with 8 min @220 V + TCEP |
| 8 | Run 7, disc deproteinized with 12 min @220 V + TCEP |
| 9 | 10 uL loading control B, equivalent to ~0.11 uL of whole blood |
| 10 | 20 uL of loading control C, ~9 ug proteinase K |
| 11 | 10 uL of Lonza catalog # 193837 quadcolor protein marker |
| 12 | 10 uL of Run 3, disc incubated with SDS |
| 13 | None |
| 14 | 5 uL of Run8, disc with no deproteinization |
| 15 | 5 uL of loading control A, ~0.26 uL whole blood |

Figure 9A:
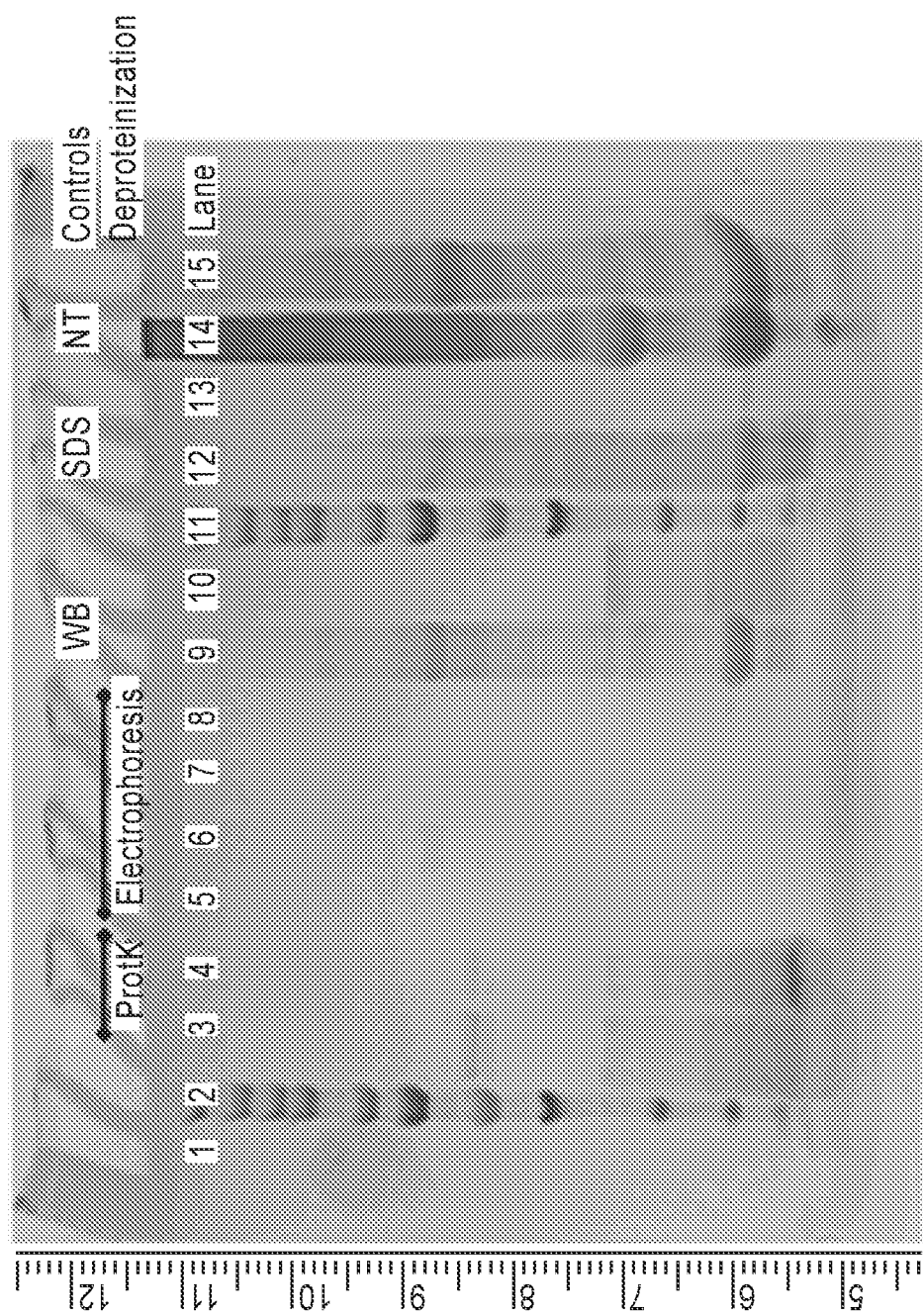
FIGS. 9A and 9B show examples of the rapid deproteinization of whole blood embedded in agarose sample plugs by electrophoresing the agarose plugs in sodium dodecyl sulfate (SDS) buffers according to some embodiments.
Figure 9B:
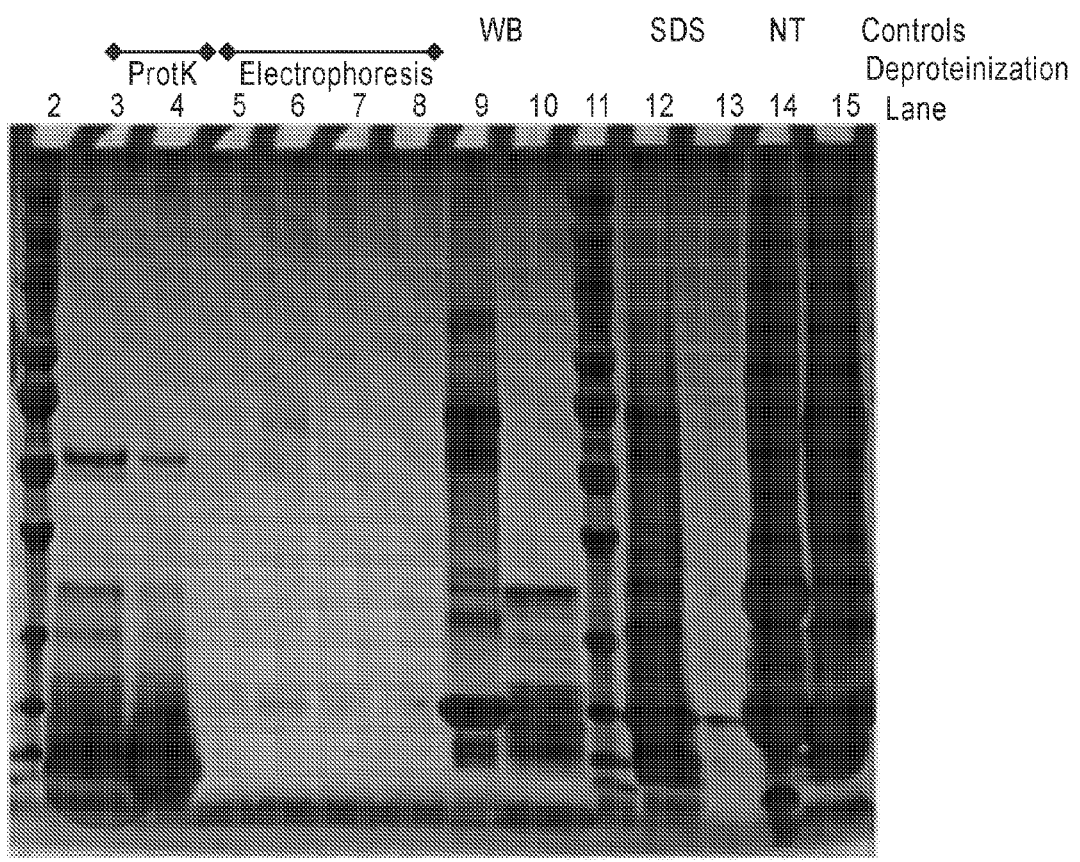

FIG. 9A shows the Coomassie stained SDS PAGE gel. Lane 9 is ~0.1 uL untreated whole blood. Lane 14 is a whole blood/agarose disc with no treatment (gel loading equivalent to ~0.26 uL of whole blood).
Lanes 3 and 4 show discs deproteinized by incubation with detergent and proteinaseK only (no electrophoretic removal of protein); the proteinase K mixture used for digestion by itself is in lane 10.
Lanes 5-8 show disc deproteinized with electrophoresis.
FIG. 9B shows the same gel, enhanced to show the faint bands.

Results

FIGS. 9A and 9B show that whole blood embedded in agarose sample plugs can be rapidly deproteinized by electrophoresing the agarose plugs in SDS buffers (FIGS. 9A and 9B, lanes 5-8). The reduction in protein content of the sample plugs is at least 100× (compare lanes 5-8, with lane 14).

It is important to recognize that the electrophoretic conditions used for deproteinization were similar to those used for the Trial 1 sample in Example 1. As shown above in Example 1, the DNA from the unrestricted electrophoretically deproteinized samples ("TE" samples in FIGS. 8A and 8B) was too large to be electrophoresed from the gel sample plugs (much larger than 250 kb under the electrophoresis conditions used for FIG. 8). Thus, it is possible to find conditions under which DNA from agarose-embedded blood cells can be rapidly purified by electrophoresis under conditions where the DNA remains in very high molecular weight in the gel sample plug. Moreover, the vast majority of the DNA molecules appear to be intact double-stranded DNA as assessed by their ability to be processed by a variety of restriction enzymes.

Electrophoretic Sample Preparation

In some embodiments, a method is provided for sample preparation which decreases the cost by physically subtracting human DNA from the sample before library construction. In such embodiments, up to 90% or more of the nucleic acid from the sample may be removed, resulting a reduction in the amount of sequencing per sample required (and therefore, decreasing the sequencing cost per sample proportionally). Accordingly, in some embodiments provide a fast and scalable method for subtraction of WBC DNA from whole blood samples.

Rapid Purification of HMW DNA from Whole Blood Using an Electrophoretic Lysis Method FIGS. 10A-G show cross section views of a disposable cassette device (1), according to some embodiments, which comprises a plastic container (2), filled with electrophoresis buffer (5), and an electrophoresis gel matrix (3) suitable for separation of macromolecules. The gel portion of the cassette also has a sample well (6), which is isolated from the electrophoresis buffer chambers on either side by the gel. As shown in the schematic top view of FIG. 10H, the gel portion (3) fills the cassette container (2) laterally, thereby creating two isolated buffer chambers (5) on either side of the gel.

Gel materials may include starch, agar, agarose, and polyacrylamide, although many other matrices with similar properties may also be used. In some embodiments, the gel material is agarose.

In general, electrophoresis buffers that are commonly used for DNA and protein electrophoresis within the pH range of 7-9 may be used. For specific embodiments (described below) that involve enzymatic processing of samples, buffers with specific pHs and ionic compositions may be used.

For embodiments using pre-filled gel cassettes, buffers that have high buffer capacity at relatively low ionic strength may be used. In this aspect, the buffers (and buffer design principles) described by Liu, Li, and Sommer (Anal. Biochem. 1999, v270, pp 112-122) are among the formulations.

The electrophoresis buffer may have EDTA as a chelating agent, which may limit the nuclease activity during the purification process. In some embodiments, high concentrations of EDTA (5-50 mM) may be beneficial to quickly kill nucleases in cell lysates, however, at least 1 mM EDTA may be used in the electrophoresis buffers. In some embodiments, less than 1 mM EDTA may be used.

To apply an electrophoretic voltage across the cassette, electrodes (4) may be inserted into the buffer chambers on either side of the gel. The electrodes may be disposable components of the cassette, or they may be reusable parts of an instrument designed to hold and run the disposable cassettes. Examples can be found in U.S. Pat. Nos. 8,361,298 and 8,361,299, as well as U.S. Patent Publication Nos. 2014/0284213 and 2015/0101932, all of which are herein incorporated by reference in their entireties.

Figure 10A:
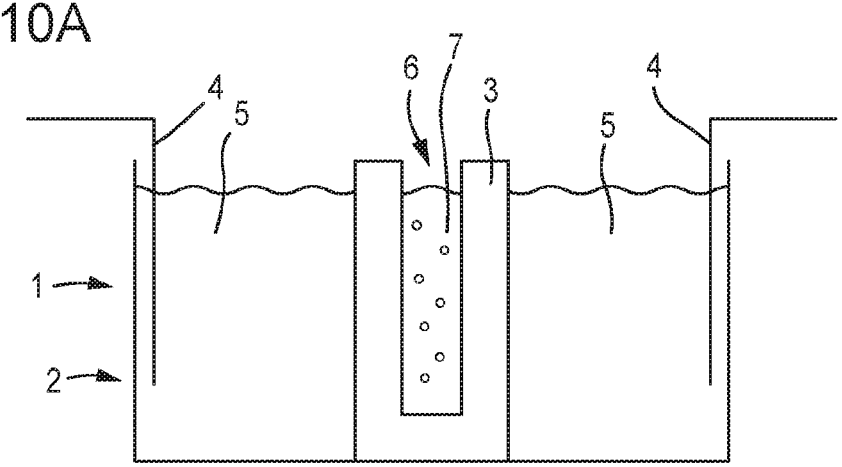
FIGS. 10A-G show cross-sectional views of a disposable cassette according to some embodiments.
Figure 10B:
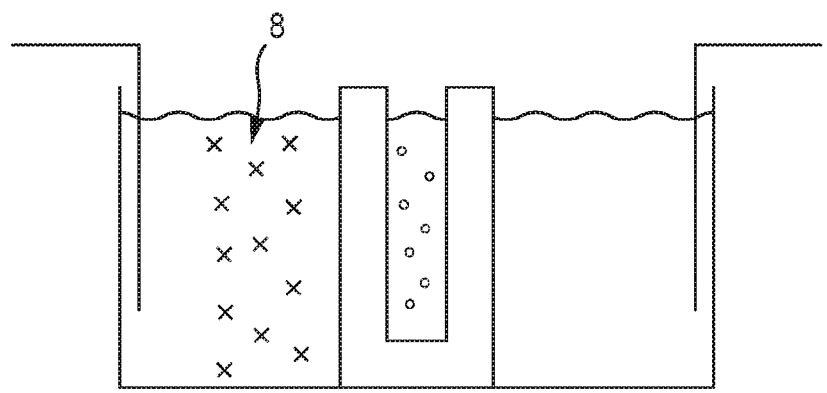

A sample may include a liquid suspension of cells. The cell suspension is loaded into the sample well (6) as shown in FIG. 10A (the circles symbolize the cells). The sample composition is densified so that the cells and loading solution have approximately the same density. This helps keep the sample evenly distributed throughout the sample well volume, by preventing the cells from settling or floating in the well during processing.

The sample composition may be configured to be isoosmotic for the cell sample so that lysis of the cells does not occur prior to electrophoretic induction of lysis. In addition, the ionic strength of the sample may be kept low so that electrophoretic heating can be kept to a minimum during processing. In some embodiments, the ionic strength of the sample may be approximately equal to that of the electrophoresis buffer.

Prior to initiating the purification process, lysis reagents (8, FIG. 10A) may be added to one of the two electrophoresis buffer chambers. The lysis reagents may be anionic detergents such as SDS at concentrations between about 0.1 and about 10% (wt/vol). Other lysis reagents may be used, including a mixture of anionic detergent and detergent-compatible proteases, such as SDS and proteinase K (such as proteinase K with a concentration range of about 50 to about 10000 ug/ml).

In some embodiments, the lysis reagents may be added after sample loading and just prior to initiation of the electrophoresis process, so that the lysis reagents will not have time to diffuse across the gel barrier between the electrophoresis buffer chamber and the sample well. This order of processing helps ensure that sample lysis and electrophoretic purification of the HMW DNA occur in a rapid, synchronous fashion.

Figure 10C:
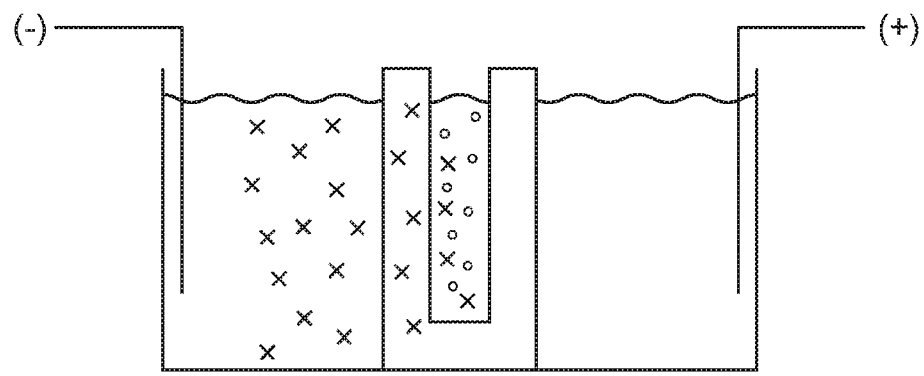
Figure 10D:
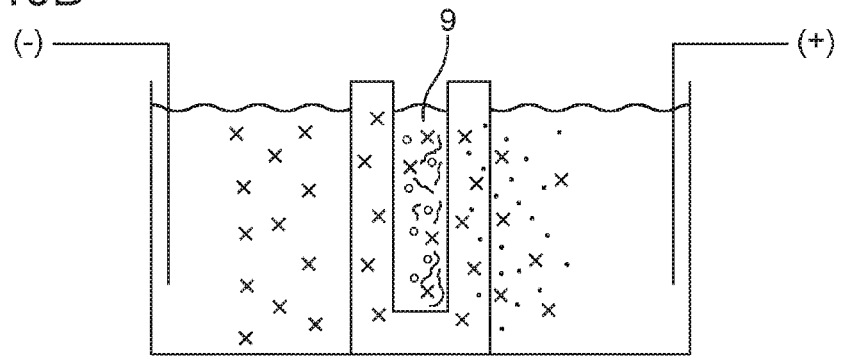

To initiate the purification process, electrophoresis voltage is applied across the cassette as shown in FIGS. 10C-10D, so that the lysis reagent is driven through the gel into the sample well, where the reagent stimulates cell lysis. The lysis reaction takes place with no mixing and no viscous shear forces, enabling the recovery of very HMW DNA molecules. A high concentration of EDTA may be used in the electrophoresis buffer and sample loading solution to chelate divalent ions, and thereby prevent nuclease activity during cell lysis.

As electrophoresis continues, the extremely HMW DNA molecules accumulate and become entangled in the wall of the sample well distal to the (−) electrode. The HMW DNA molecules are too large to enter the gel under continuous or alternating field conditions, and remain on the sample well wall. Under the conditions used for the examples below, the entangled, immobilized HMW DNA molecules appear to be >2 megabases in size, as estimated by analytical pulsed field gel electrophoresis.

Figure 10E:
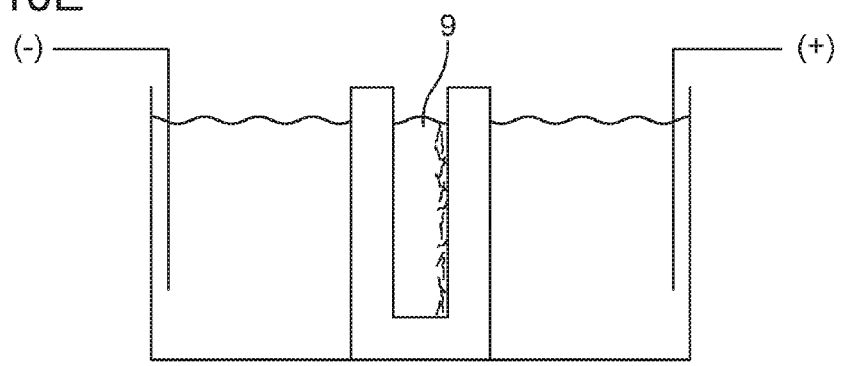

During the electrophoretic lysis process, all other charged species, including cellular proteins, lysis reagents, lipids in detergent micelles, and salts are electrophoresed rapidly out of the sample well. Most will be moved to the (+) electrode as complexes with anionic lysis detergents such as SDS, as shown in FIG. 10E.

Figure 10F:
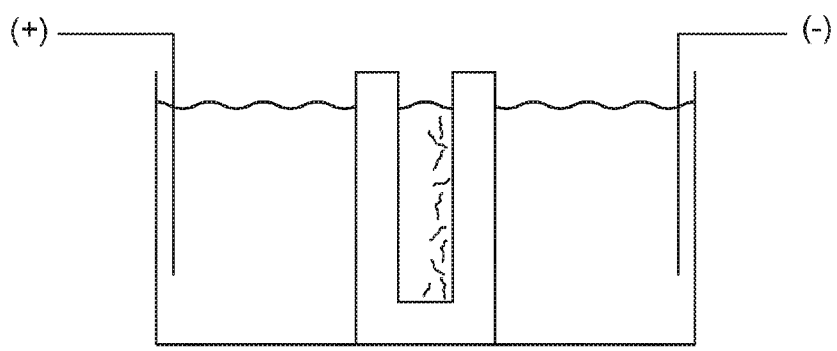
Figure 10G:
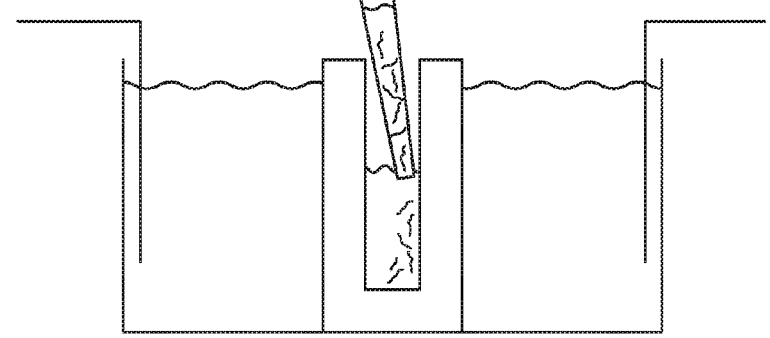
Figure 10H:
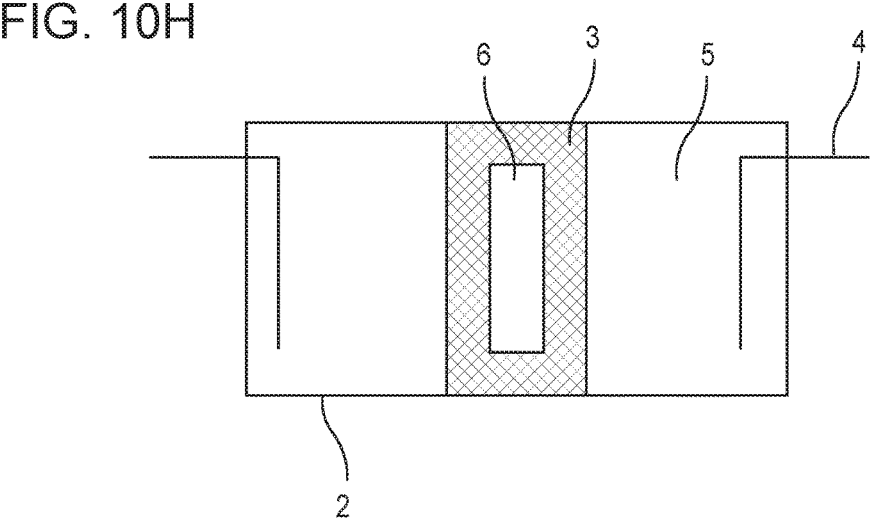
FIG. 10H shows a top view of a disposable cassette according to some embodiments.

There are several ways to recover the purified HMW DNA fraction, including the method shown in FIG. 10F-10G (for example). The contaminants are removed from the cassette by exchanging the buffer in the reservoirs. A reversed field voltage is applied to the cassette to move the HMW DNA off of the wall of the sample well. The conditions for this reversed field electrophoresis are calibrated carefully for each cassette and gel type, since the DNA can become entangled on the opposite wall if the electrophoresis is allowed to continue too long. The liberated DNA can then be removed from the sample well in liquid electrophoresis buffer by automated or manual pipetting means (FIG. 10G).

Figure 11:
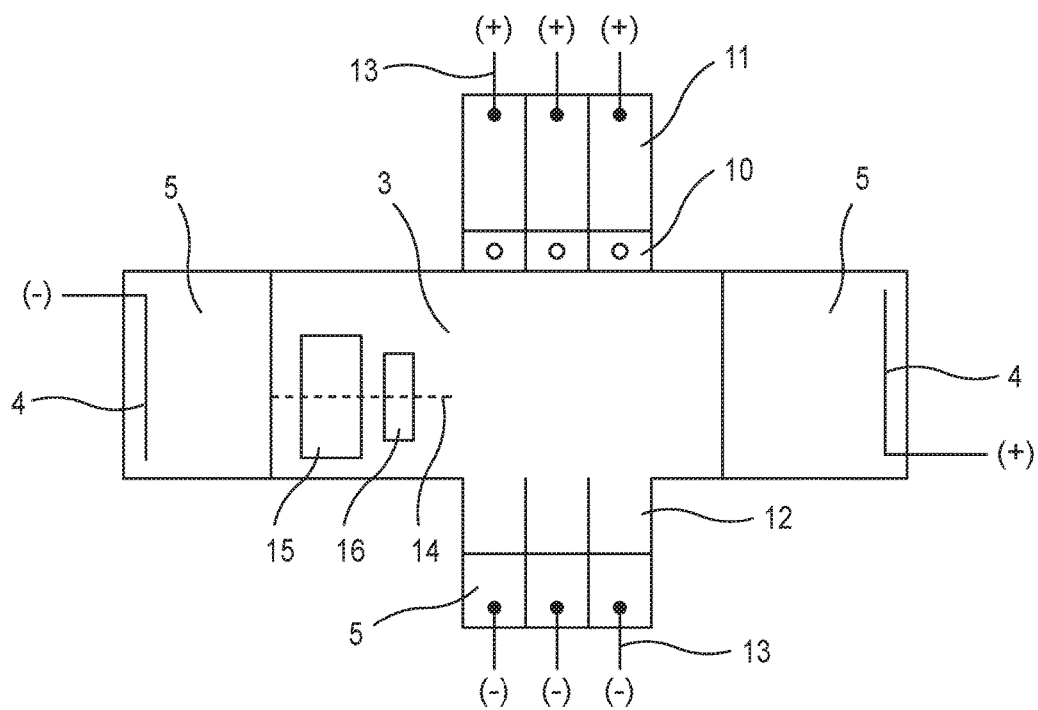
FIG. 11 shows a top view of the cassette according to some embodiments.
Figure 12A:
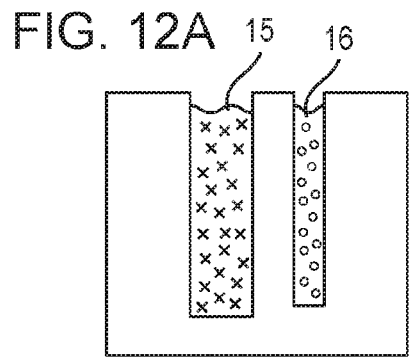
FIGS. 12a-h show side views of reagent and sample wells of a cassette according to some embodiments.
Figure 12B:
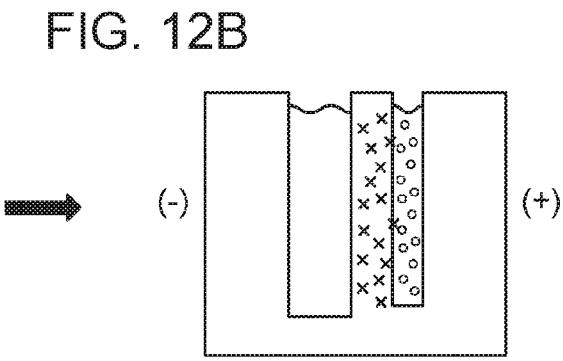
Figure 12C:
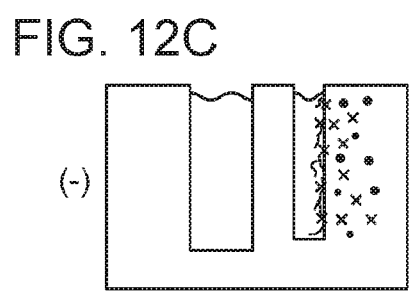
Figure 12D:
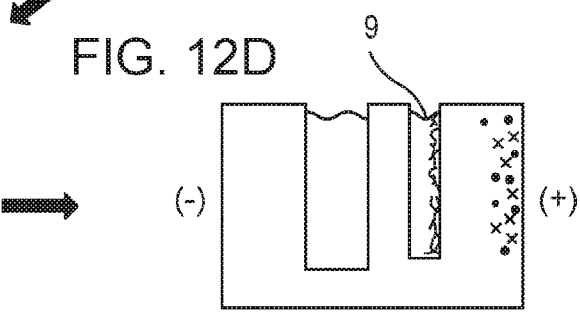
Figure 12E:
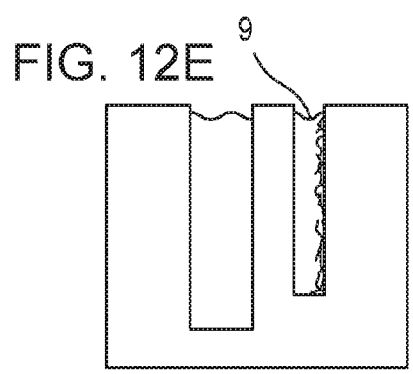
Figure 12F:
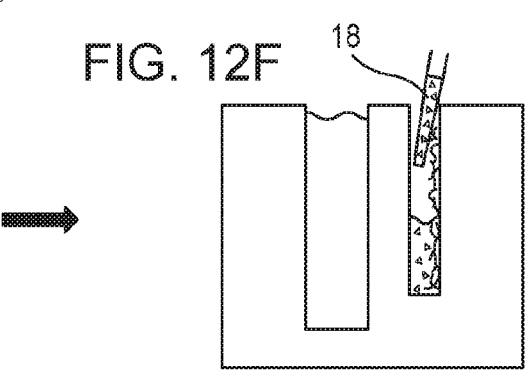
Figure 12G:
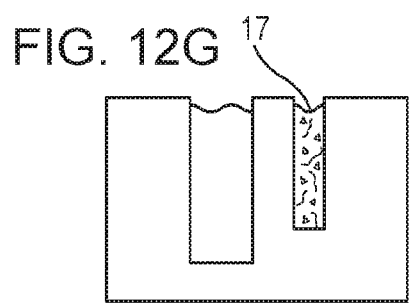
Figure 12H:
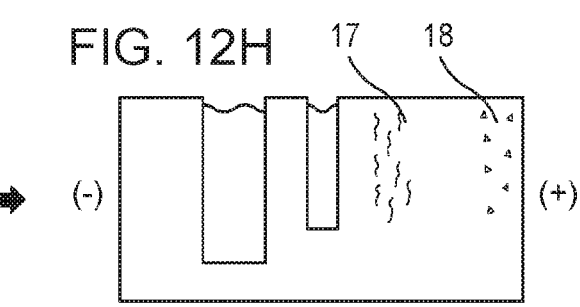

Processes and Devices for Automated Electrophoretic DNA Extraction and Enzymatic Processing The disposable cassette of FIG. 11 (showing a top view of the cassette; see also U.S. Patent Publication No. 2015/0101932), in addition to a sample well (16), the cassette includes a reagent well (15) upstream of the sample well. The reagent well may be located between the sample well and the (−) separation buffer chamber. Also included are separation electrodes (4) that can move negatively charged analytes like DNA from one direction to the other; and when desired separation of analytes has been accomplished, the separation electrodes are turned off, and elution channel electrodes (13) are activated to move the separated negatively charged analytes upward into buffer-filled elution modules (10). The elution modules are sealed on the (+) electrode side with a PES ultrafiltration membrane (cutoff 10 kDa) which will retain genomic DNA molecules inside the elution modules.

FIG. 12 displays functions of the reagent and sample wells (15, 16, FIG. 11), as viewed along the sagittal section of the cassette indicated by the dotted line, 14, in FIG. 11. FIG. 12A shows the sample well (16) filled with a cell suspension and the reagent well filled with a negatively charged lysis reagent, such as SDS. FIG. 12A shows the configuration of the wells just prior to activating electrophoresis voltage. FIGS. 12B, 12C, and 12D show the state of the wells after activation of electrophoresis. In FIG. 12B, the reagent is moving into the sample well to initiate cell lysis. In FIG. 12C, lysis is almost complete; HMW DNA is accumulating on the (+) face of the sample well, and contaminants and lysis reagents are being electrophoresed rightward into the separation gel, toward the (+) separation electrode. In FIG. 12D, highly purified HMW DNA (9) is entangled on the sample well wall, and contaminants are moving further away rightward from the sample well. As described for FIG. 10E above, the DNA (9) is firmly attached to the (+) wall of the sample well. The electrophoresis buffer can be removed from the sample well without disturbing the gel-entangled DNA layer, as shown in FIG. 12E, and the sample well can be refilled, either manually or automatically, with buffer containing DNA modification enzymes (18), as shown in FIG. 12F.

Figure 13A:
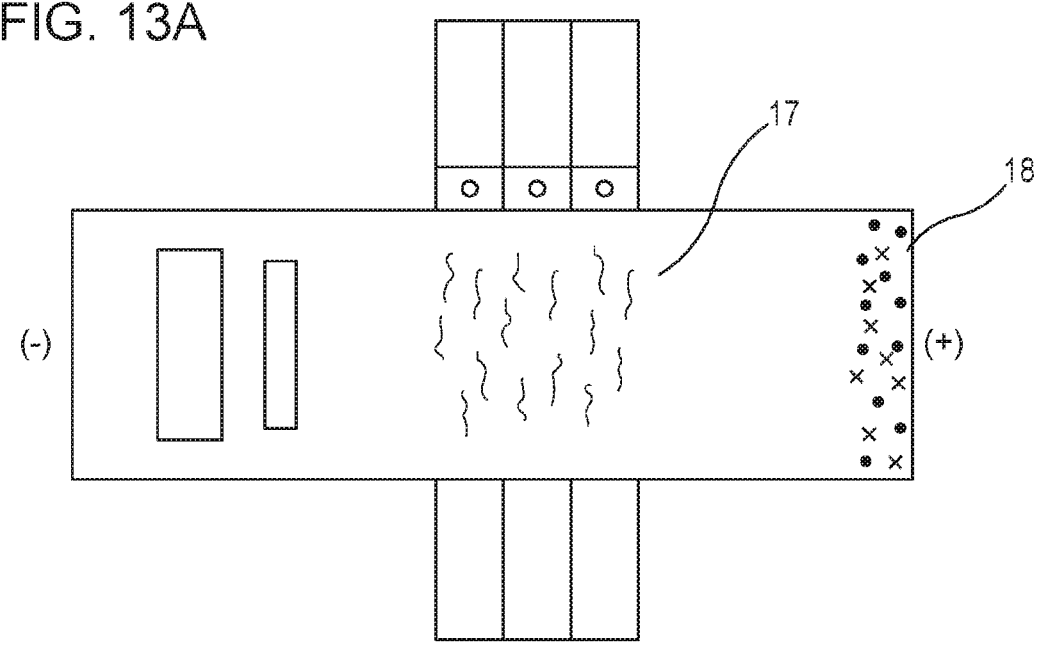
FIGS. 13A-B show top views of the cassette according to some embodiments.
Figure 13B:
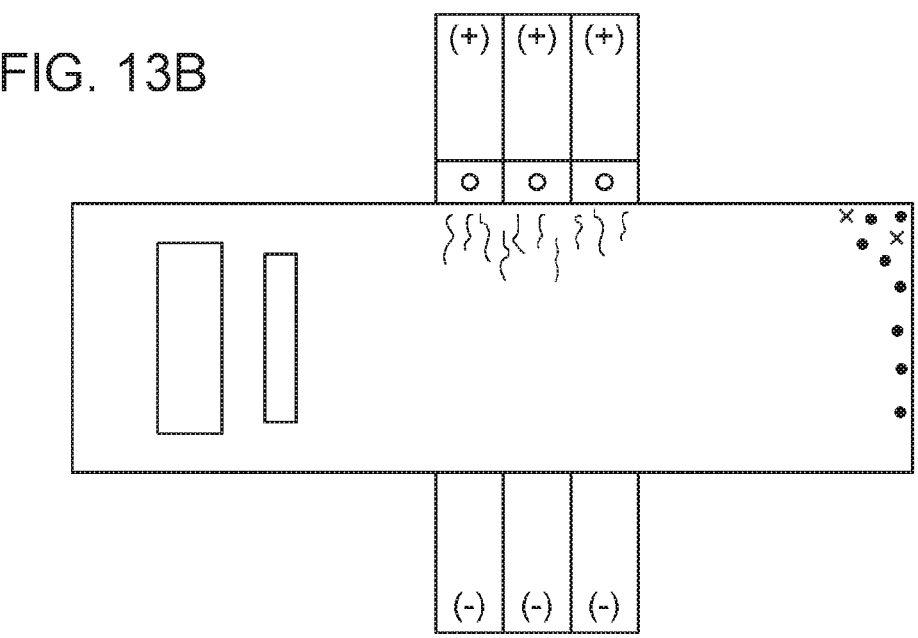

The enzymatic treatment shown in FIG. 12 involves controlled cleavage of the immobilized HMW DNA by a double-stranded endonuclease in order to produce randomly-fragmented HMW DNA with a size distribution in the 100 kb-1000 kb range. After an incubation period, such as a period of time sufficient to produce the desired size distribution, the separation electrodes are reactivated, and the processed DNA fragments (17) are electrophoresed out of the sample well and rightward into the separation channel. The nuclease used for processing can be inactivated by addition of SDS to the sample well, or to the reagent well before initiating the separation electrophoresis. The SDS-denatured processing nuclease (18) migrates far ahead of the much-larger processed DNA fragments, as shown schematically in side view in FIG. 12H. FIG. 13A shows a top view of the cassette after the separation electrophoresis stage shown in FIG. 11H. At this stage, the processed DNA fragments are positioned in front of the elution channels. The separation electrodes are deactivated, and elution electrodes are activated, thereby electroeluting the processed DNA from the separation gel into the buffer-filled elution modules (as shown schematically in FIG. 13B), where the processed DNA can be recovered manually or automatically.

In some embodiments, reagents for release of immobilized HMW DNA from the sample well include non-specific double-stranded endonucleases, such as DNase I in the presence of Mn++ ions, and Fragmentase (New England Biolabs). Other reagents may also be used, such as transposases that have been loaded with synthetic oligonucleotide adapter duplexes, examples of which include the mutant Tn5 transposase, Nextera (Illumina), the mutant Tn5 transposase produced by Kapa Biosystems, and the mutant Mu transposase reagent, MuSeek, (Thermo Life). Other reagents include restriction endonucleases. When using restriction endonucleases, digestion conditions may only allow a very limited extent of digestion, so that the released DNA products are extremely large. Especially preferred DNA cleavage reagents are restriction enzymes such as CviKI-1 (New England Biolabs), which have very low sequence specificity and are insensitive to the methylation status of the genomic DNA. Limited digestion by CviKI-1 and similar low specificity enzymes may produce a nearly random set of cleavage sites.

The schematic workflow of FIG. 12 can also be used for NGS library construction using transposase-based reagent systems like Nextera (Illumina). In such workflows, transposase molecules, carrying sequencing adapters attached to transposase binding sites, are reacted with genomic DNA. The transposase reaction simultaneously fragments the genomic DNA and attaches the sequencing adapters to the ends of the fragmented genomic DNA. Transposase reagents for NGS library construction are available commercially from Illumina (Nextera, based on a mutant Tn5 transposase) and Thermo Fisher (MuSeek kits, based on Mu transposase). A transposase-mediated library workflow may work similar to the one shown in FIG. 12, provided that the enzyme (18) used in FIGS. 12F-G was a suitable transposase loaded with specialized sequencing adapters. In this way, the workflow shown in FIGS. 12 and 13 is capable of producing an NGS library directly from a whole blood sample, using a single disposable cassette, three or four automated liquid handling steps, and a simple programmable electrophoresis power supply.

It should be noted that HMW DNA, when immobilized on the surface of an agarose sample well by electrophoretic entanglement, can be used to perform a variety of other enzymatic and chemical modification reactions on the HMW DNA. In general, the reversible immobilization of the HMW DNA on the sample well wall provides a convenient aqueous support that is well suited to serial enzymatic treatments of the DNA. In principle, any set of treatments that does not reduce the size of the DNA so much that it becomes disentangled from the support can be performed by exchanging the reagent mixture in the sample well. In some embodiments, electrophoretic purification may be performed between reaction steps to remove residual charged reaction components out of the sample well and into the separation gel.

As a non-limiting example, fluorescent labeling of DNA at sequence-specific nicking endonuclease sites, a process used in optical mapping of HMW DNA (for instance, see the Bionano Genomics workflow), may be an alternative processing workflow. After electrophoretic purification of the HMW DNA, as described above and in FIG. 12, the sample well may be refilled with a DNA repair mix to seal all random nicks introduced during the purification reaction. After repair, the sample well may be emptied, rinsed, and refilled with a reaction mix containing a nicking endonuclease that introduces single-stranded nicks at specific base sequences (see From NEB expressions July 2006, vol 1.2, By Siu-hong Chan, Ph.D. and Shuang-yong Xu, Ph.D., New England Biolabs, Inc; https://www.neb.com/tools-and-resources/feature-articles/nicking-endonucleases-the-discovery-and-engineering-of-restriction-enzyme-variants, which is hereby expressly incorporated by reference). After nicking, the sample well may be emptied, rinsed, and then refilled with a mixture of Taq DNA polymerase and fluorescent nucleotides in a suitable buffer. After raising the temperature of the gel cassette to around 50° C., the polymerase may carry out nick-translation reactions at the nicking sites, thereby fluorescently labeling the sequences at nick sites for optical mapping. Throughout the nicking and labeling reactions, the DNA may still be in HMW form, and may still be entangled with the agarose well wall. After the labeling reaction, the DNA may be lightly fragmented by a non-specific double-stranded endonuclease, as described above and in FIG. 12, and purified electrophoretically as described above and in FIGS. 12 and 13.

The schematic workflow of FIGS. 12A-D, may also be used for physical subtraction of intact genomic DNA, such as in support of NGS diagnostic methods that seek to detect infectious pathogens through detection of non-human sequences clinical samples. For instance, using the workflow shown in FIGS. 12A-D, virtually all undamaged human sequences from a blood sample may be trapped, immobilized on the (+) wall of the sample well. Smaller pathogen DNA genomes (<800 kb in size to ensure entry into the gel) and all RNA molecules (host and pathogen) may remain electrophoretically mobile and may migrate out of the sample well. These smaller molecules may be electroeluted and recovered for NGS library preparation as shown schematically in FIG. 13. Because RNA molecules are smaller than genomic DNAs, and heterogeneous in size, the cassettes used for gDNA subtracted RNA may require higher agarose concentrations, and a larger elution channel region. This may offer a broader collection size range, and cassettes, such as those described in U.S. Patent Publication No. 2015/0101932 (incorporated herein by reference), may be used.

Figure 16A:
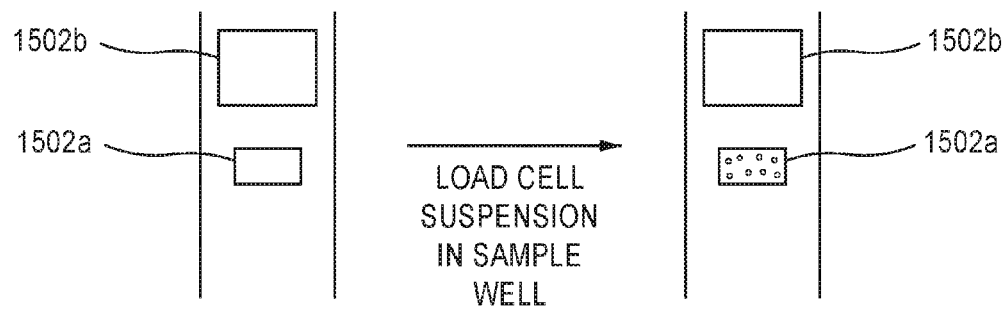
Figure 16B:
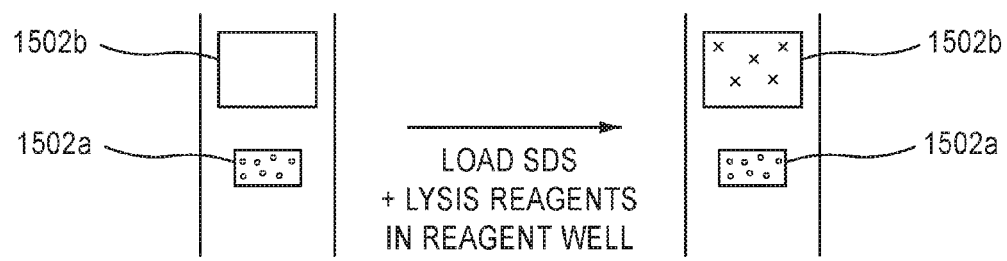
Figure 16C:
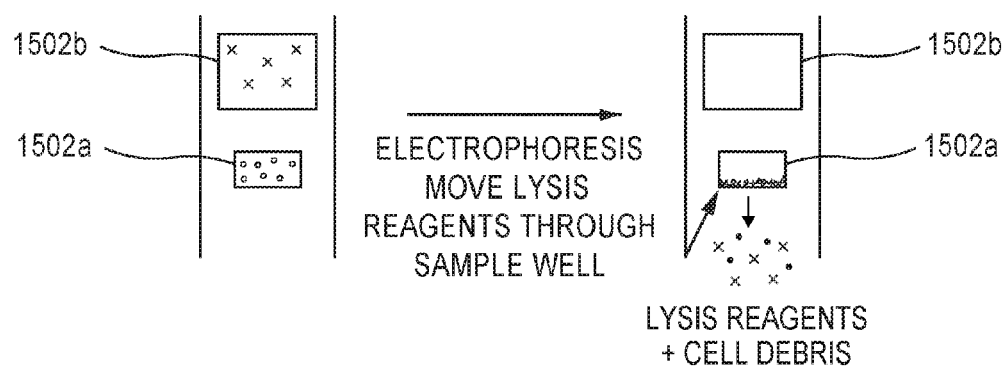
Figure 16D:
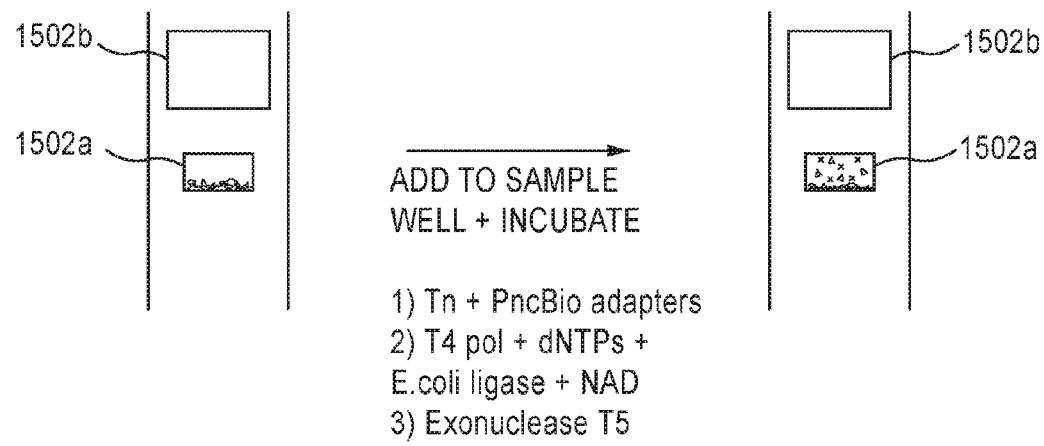
Figure 16E:
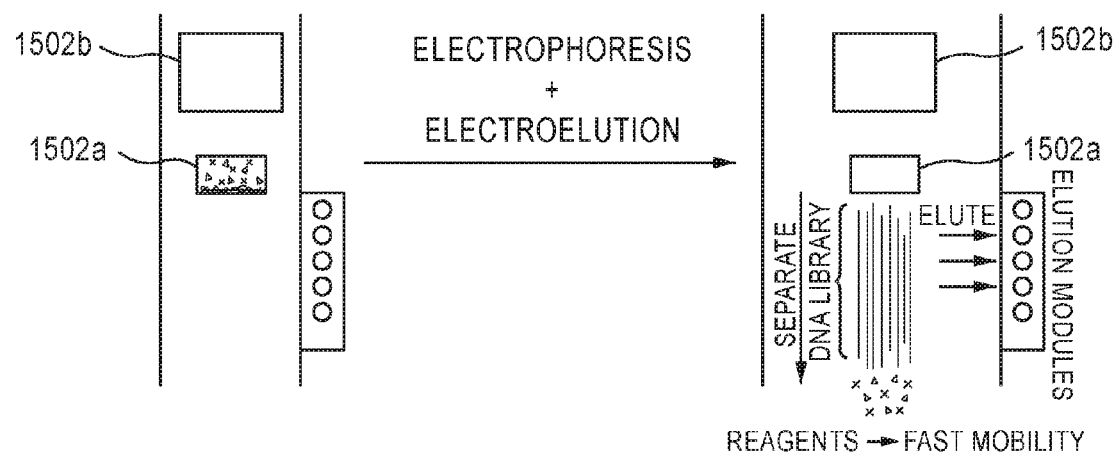
Figures 16F, 16G, 16H:
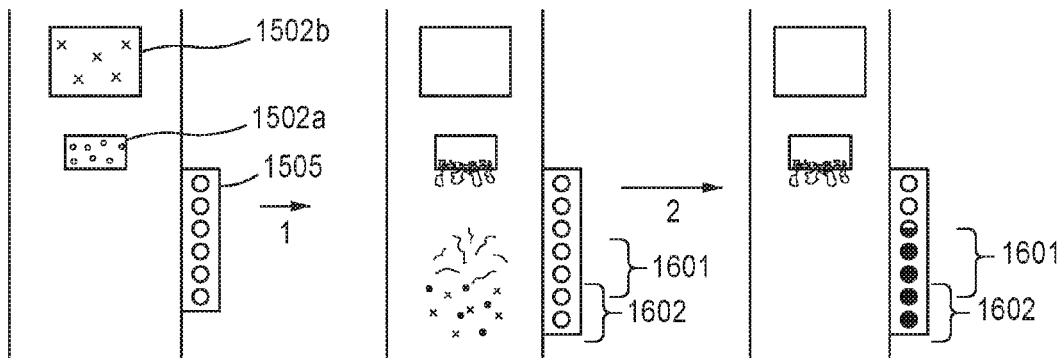
Figures 16I, 16J:
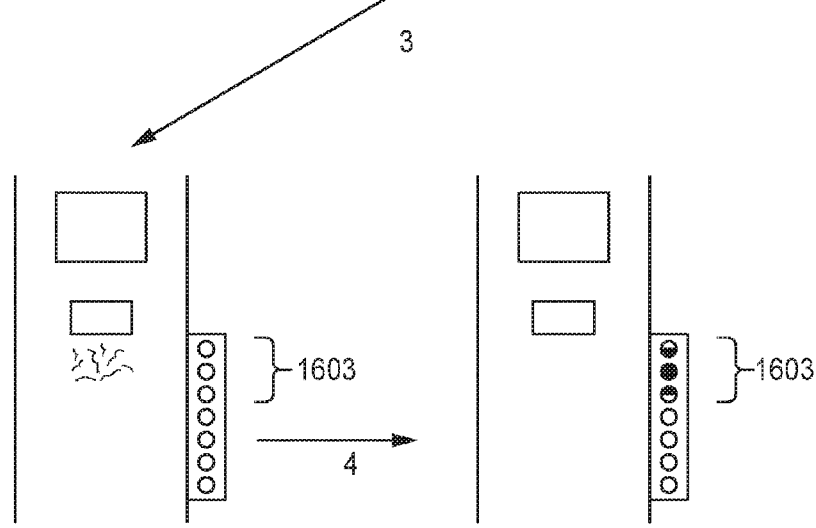

As shown in FIGS. 16F-J, in some embodiments, multiple analytes from the same sample may be purified and/or isolated. These figures show the separation gel and elution module from a similar cassette of that shown in FIG. 13. FIG. 16F shows a cassette with a cell suspension loaded in sample well (1502a) and lysis reagent loaded in the reagent well (1502b). Lysis reagents for this embodiment may be anionic detergents such as SDS at concentrations between about 0.1% and about 10% (w/v). In stage 1 (from FIG. 16F to 16F), separation electrophoresis is carried out so that negatively charged species migrate from top to bottom of the cassette. Negatively charged SDS migrates down through the sample well, lysing the cells. The HMW genomic DNA remains immobilized on the (+) side of the sample well because of its large size. However cellular RNA and SDS-coated cellular proteins are liberated from the sample well and migrate down the separation gel toward the (+) electrode. At gel concentrations of 2% and below, agarose gels have very little retardation of protein-SDS complexes. As a result, most cellular protein will comigrate with the high-mobility SDS micelles (FIG. 16G, region of bracket 1602). Most cellular RNAs are substantially larger in molecular weight, between about 600 and about 3000 bases in size (200-1000 kDa), and therefore will migrate as a partially resolved band (FIG. 16G, region of bracket 1601) just above from the SDS-protein band. Upon application of elution voltage (stage 2, from FIG. 16G to 16H), the RNA and SDS-protein fractions are eluted into the elution modules where they are recovered in electrophoresis buffer. Depending on the gel system and electrophoresis conditions, there may be some overlap between small RNA fractions (RNA below 600 bases) and the SDS-protein fractions, as suggested in the figures by the overlap between the brackets 1601 and 1602. If necessary, SDS can be removed from the electroeluted protein fractions using commercial detergent removal columns (e.g., HiPPR spin columns, Thermo Life) or acetone precipitation.

Improved resolution between fast moving nucleic acid fractions and SDS-protein complexes in multi-analyte applications of the cassette between can be achieved using a two-part separation gel. For instance, the upper portion of the gel column, including the region containing the reagent and sample wells can comprise a relatively low concentration agarose gel, for instance about 0.75% or lower, while the lower half of the gel can comprise a higher concentration agarose gel, for instance about 2% or higher, which will allow better discrimination in mobility between the detergent-protein complexes and the lower molecular weight nucleic acid fractions.

Improved resolution in multi-analyte applications of the cassette can also be achieved by the use of electrophoretic stacking, also known as isotachophoresis. In such embodiments, embodiment cassette, such as the cassette shown in FIG. 16K, in which the upper buffer chamber (FIG. 16K, 1601) is replaced at run time, with a different buffer from that contained in the gel (1610), lower buffer chamber (1602), and elution buffer channels (1609). The upper buffer may comprise an anionic detergent suitable for lysing the cell sample in the sample well (1603). In addition, the run-time upper buffer comprises an ionic composition suitable for achieving selective stacking of detergent-protein complexes, DNA, or RNA. Examples of buffer designs suitable for such stacking applications can be found in Laemmli, Nature vol 227, 680-685, 1970; Ornstein and Davis, Annal. NY Acad. Sci, 1964; Persat et al. Anal. Chem. Vol 81, pp 9507-9511, 2009; Schoch et al. Lab on a Chip vol 9, pp 2145-2152, 2009. FIG. 16L shows a schematic illustration of the cassette after electrophoretic purification and separation of a cell suspension, using a buffer system designed to stack proteins (such as, for example Laemmli, Nature vol 227, 680-685, 1970). The gel (1610), lower buffer reservoir (1602), and elution channels (1609) contain electrophoresis buffer without SDS. Just prior to sample loading, the upper buffer chamber (1601) is emptied are refilled with an SDS buffer suitable for sample lysis and electrophoretic stacking of protein-detergent complexes. Voltage is applied to the separation electrodes (1608), and the SDS migrates down into the cassette, thereby lysing the cell suspension held in the sample well (1603). The genomic DNA (1605) is trapped on the (+) side of the sample well and is immobilized there due to its large size. RNA and detergent-protein complexes are electrophoresed into the separation gel. The RNA (1606) is separated in the gel matrix on the basis of size. Because of the non-restrictive large pore size of the agarose gel, the protein-detergent complexes are stacked by the buffer system and migrate through the separation gel in a tight single band (1607) of high mobility. After separation, the RNA and protein components can be eluted as relatively pure fractions. If desired, the genomic DNA can be recovered from the sample well in a second cycle of fragmentation, separation, and elution as discussed above for FIGS. 16F-L.

In cases where preparation of protein analytes is important, the lysis reagent may comprise chemically degradable or unstable anionic detergents. Examples of such detergents include RapiGest (Waters Corp.), and MaSDeS (Chang et al., J. Proteome Res. Vol 14, pp 1587, 2015). These detergents are inactivated by incubation of the detergent-protein fractions under acid conditions (for example 10% formic acid in 25 mM ammonium bicarbonate). Such cleavable detergents may be very useful in streamlining sample prep workflows for protein mass spectrometry.

After elution and removal of the RNA and protein fractions from the cassette, the sample well and reagent well can be refilled with reagents suitable for controlled fragmentation of the HMW DNA that was left behind on the wall of the sample well. After fragmentation, the reagent well may be filled with a purification reagent, such as, for example, a buffered solution of SDS at a concentration between about 0.1% and about 10%, and a second round of purification electrophoresis may be performed to move the fragmented and purified genomic DNA out of the sample well (stage 3, FIGS. 16H-I) down to a region (FIGS. 16I and 16J, bracket 1603) where it can be eluted in pure form from the separation gel (stage 4, FIGS. 16I-J).

While the multi-analyte purification shown in FIGS. 16F-J utilizes two separation electrophoresis steps and two electroelution steps to produce purified genomic DNA, RNA, and protein from the same sample. In other embodiments, where only RNA and protein fractions from the same sample are required, or where only DNA and RNA fractions from the same sample are required, an inventive process involving only a single separation and elution cycle may suffice.

Cassette with Lysing Reagent Sample Well

Figures 14A, 14B:
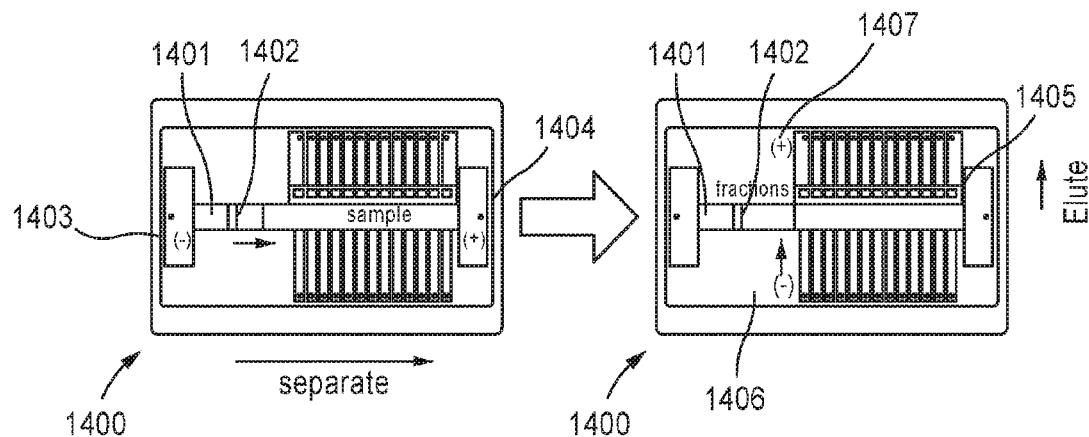
FIGS. 14A-B show top views of a cassette according to some embodiments.

FIGS. 14A-B show top views of an exemplary cassette 1400, having a central sample gel channel 1401, a sample well 1402, sample channel electrophoretic electrodes 1403 (negative) and 1404 (positive). As shown in FIG. 14A, the electrodes are used to electrophoretically drive a sample (initially contained in sample well 1402), along the channel 1401 towards the positive electrode 1404. FIG. 14B illustrates the collection of different fractions of the sample (e.g., fractions of DNA) into receiving areas 1405 via electrophoresis between negative electrodes 1406 (negative) and 1407 (positive).

Figure 15A:
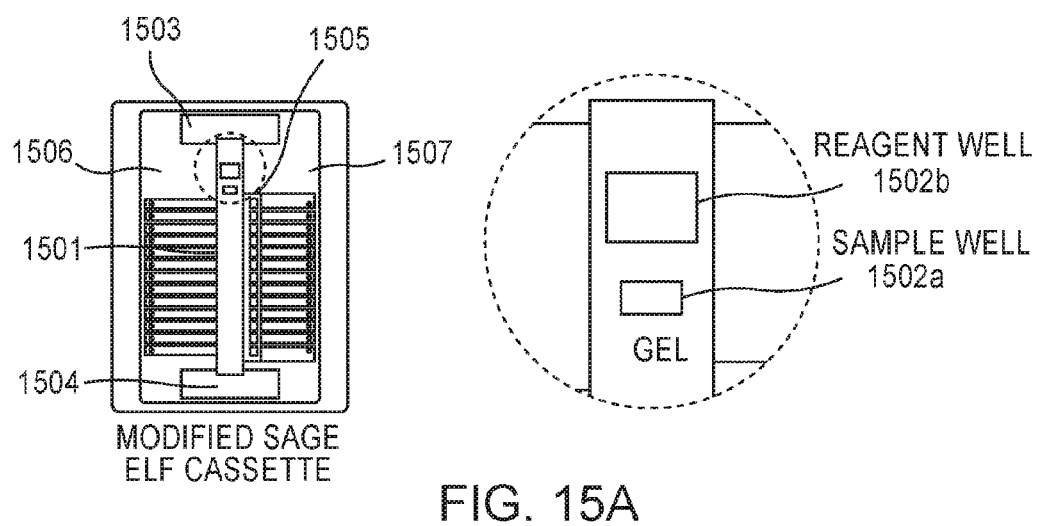

In some embodiments, as shown in FIG. 15A, a cassette is provided which includes a central gel channel 1501, a sample well 1502*a*, a reagent well 1502*b*, primary electrophoretic electrodes 1503 (negative) and 1504 (positive), fraction receiving areas 1505, and secondary electrophoretic electrodes for each receiving area 1506 (negative) and 1507 (positive). An exemplary embodiment of the cassette of FIG. 15A is shown in FIG. 15C. This embodiment is based on the cassette of published US application no. 201150101932 (which is hereby incorporated by reference in its entirety), currently sold under the name SageELF (Sage Science).

FIG. 15B, shows the upper part of the SageELF cassette, and FIG. 15C shows the modified version, in which the sample well has been moved closer to the elution module region, and a larger volume reagent well has been provided upstream (proximal to the negative separation electrode) of the sample well. FIGS. 16A-E illustrate a workflow in creating a DNA library according to some embodiments using the cassette of any of FIGS. 15A-C (for example). As shown in FIG. 16A, a cell suspension may be loaded in the sample well 1502*a* of the cassette, and additionally, SDS and/or a lysis reagent(s) may be loaded into the reagent well 1502*b*. Upon placing a voltage bias across the primary electrodes 1503/1504, the lysis reagent(s) are electrophoretically driven into and/or through the sample well (FIG. 16C). Once into the sample well, the lysing agent(s) breaks down the cells within the sample well, and continue progression along the gel. DNA, however, remains substantially immobilized within the sample well (e.g., on the wall) since DNA molecules are too large to enter the gel. As the cells are broken down, cell debris also is driven along the gel by electrophoresis.

Upon completion of the lysing process, the following is added, sequentially, to the sample well (see FIG. 16D):
Tn and PacBio adapters (and incubate);
T4pol, dNTPs, *E. coli* ligase, and NAD (and incubate);
Exonuclease T5 (and incubate).

In some embodiments, these incubations are performed sequentially (as indicated), however in other embodiments, the incubations may be performed concurrently and/or not all of these incubations may be used.

As shown in FIG. 16E, electrophoresis and/or electroelution enable size-selection to product a DNA library from the sample.

Other Examples According to Some Embodiments of the Disclosure

Example: Electrophoretic Extraction of Genomic DNA from Whole Goat Blood

A 2% agarose gel (SeaKem Gold, Lonza) was cast in 10 mM Tris-HCl, pH 7.6. The gel was approximately 11 mm thick, with sample wells 1.5 mm thick×7 mm deep×11 mm wide. The gel was placed in a minigel box containing 0.5×KBB buffer (1×KBB=50 mM Tris, 37 mM TAPS, 0.08 mM EDTA, pH 8.7) with additional 5 mM EDTA and 1% SDS. The gel was immersed so that the surface of the gel was not submerged below the buffer (so that the sample well contents were not in fluid contact with the buffer in the reservoir); the buffer covered about 75% of the height of the gel at its edges. After the gel was placed in contact with the electrophoresis buffer, the samples were loaded as quickly as possible and the electrophoresis power was activated. Samples in each lane were 20 ul fresh whole goat blood (anticoatulated with ACD, Lampire Biologicals) mixed with 80 ul of TBSEG (50 mM Tris-HCl, pH 7.6, 150 mM NaCl, 5 mM EDTA, 10% glycerol).

Figure 17A:
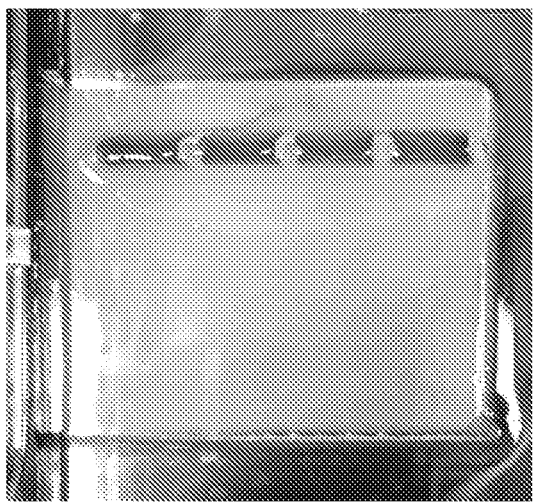
FIGS. 17A-C show gel before, during, and after an electrophoretic extraction according to some embodiments.
Figure 17B:
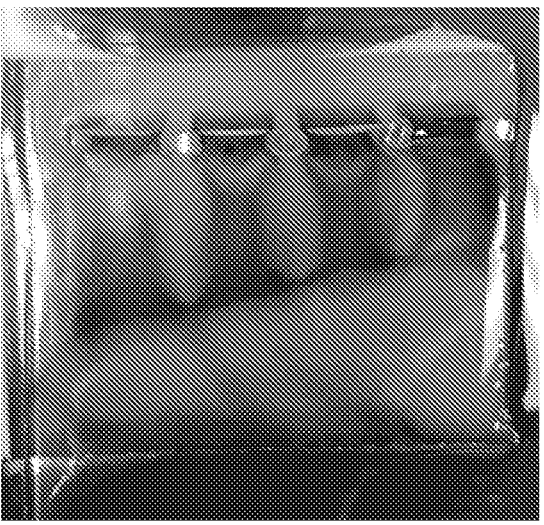
Figure 17C:
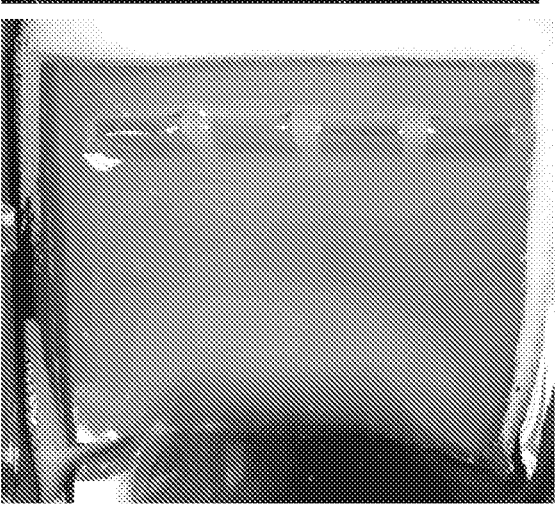
Figure 18A:
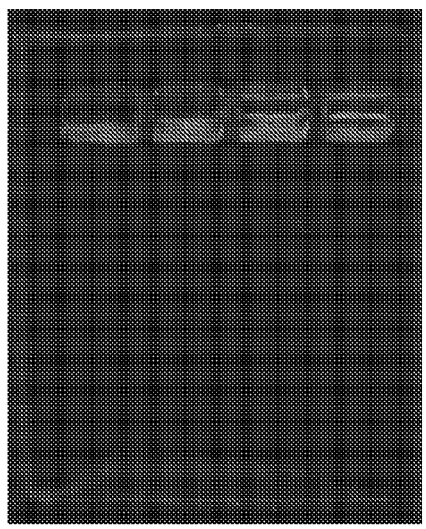
FIGS. 18A-D show the gel in various stages after electrophoretic extraction according to some embodiments.

FIG. 17A shows the gel just before starting the electrophoretic extraction. The electrophoretic extraction was carried out at 10V/cm for 35 minutes. FIG. 17B shows the appearance of the gel after 7 minutes of electrophoresis, and FIG. 17C shows the gel at the end of the 35 minute extraction process. The gel was removed from the minigel box and rinsed briefly in 200 ml of 0.5×KBB without SDS, and then stained with 0.5 ug/ml ethidium bromide in 0.5× KBB for 20 minutes. FIG. 18A shows the image of the ethidium-stained gel immediately after electrophoretic extraction (no further treatment). A heavy band of DNA on the (+) side of the sample well is seen in all lanes. The ethidium stained gel was rinsed briefly with 0.5×KBB, the sample wells were emptied and refilled with the following:

Lane 1—Generic restriction buffer only

Lane 2—Generic restriction buffer+50 units of HindIII (NEB)

Lane 3—Generic restriction buffer+50 units of SalI (NEB)

Lane 4—0.5×KBB (electrophoresis buffer without SDS)

Generic restriction buffer is 50 mM Tris-HCl, pH 7.6, 100 mM NaCl, 10 mM MgCl2, 100 ug/ml hydroxypropyl cyclodextrin.

Figure 18B:
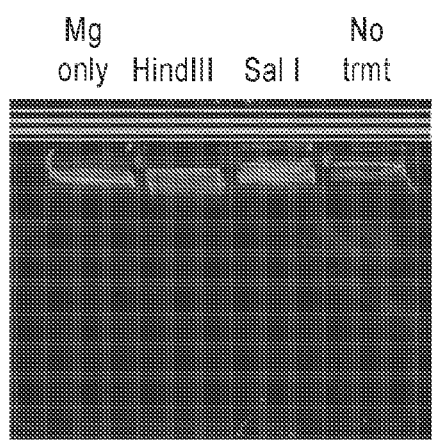
Figure 18C:
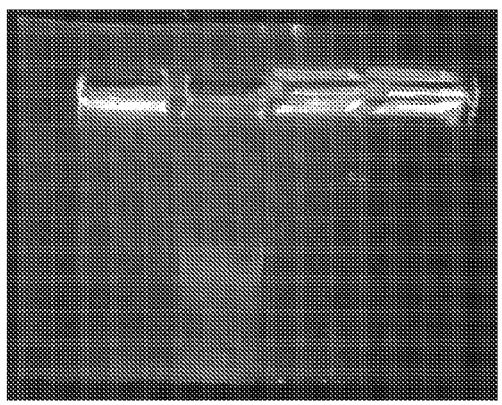
Figure 18D:

After incubation of gel at room temp for 15 minutes, the gel was immersed (but not submerged) in 0.5×KBB and electrophoresed 10V/cm for 15 minutes. The gel was restained in ethidium bromide as before and the resulting image is shown in FIG. 18B. Lanes 1, 3, and 4 look unchanged from FIG. 18A showing that the HMW DNA on the lower sample gel wall was not altered by exposure to $Mg^{++}$, or SalI. The absence of cleavage in the $Mg^{++}$ lane demonstrates that the HMW DNA entangled on the surface of the sample well is substantially free of nuclease contamination. Lane 2, digested with HindIII, shows some increased mobility of the DNA, as if some cleavage had occurred. The gel was electrophoresed for an additional hour, restained, and the image 6c shows a top view of the gel, while 6d shows an oblique view—looking up toward the sample wells from a position below the bottom end of the gel, to better show the a cross-section view of the sample wells. As seen in FIGS. 18C-D, most of the DNA in well 2 was digested into fragments small enough to enter the 2% gel by HindIII. This demonstrates that the HMW DNA immobilized on the sample well is accessible to DNA processing enzymes Example: Rapid Electrophoretic Preparation of HMW DNA from Goat WBCs Followed by in-Well Reaction of Extracted DNA with Mutant Tn5 Transposase Preparation of Agarose Gel:

An agarose solution was prepared by adding to 4 grams of SeaKem gold agarose (Lonza) 385 grams of water and 10 mL of 1M Tris Acetate, pH 7.5 and 80 uL of 0.5M disodium EDTA; the solution was microwaved until the agarose was fully dissolved, and the solution was then kept in a water bath at 70° C.

Figure 19A:
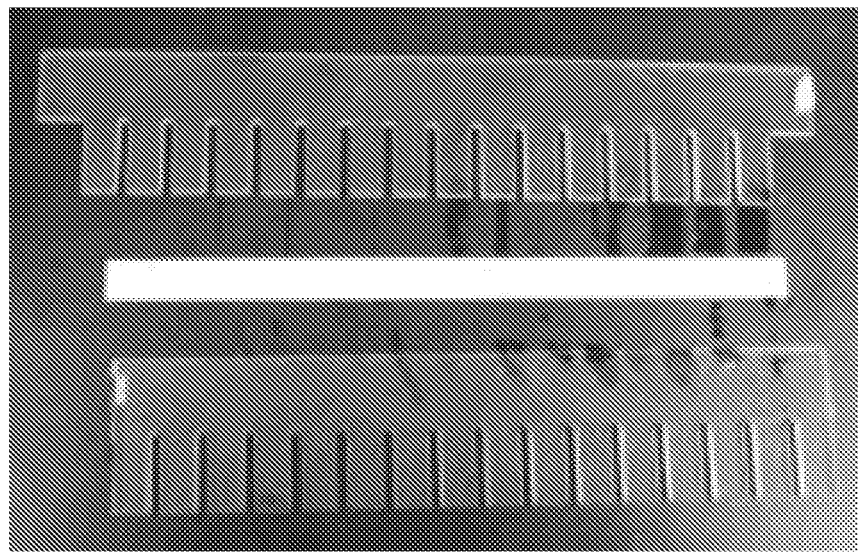
FIG. 19A shows a comb to create rows of wells according to some embodiments.

A comb that creates two rows of 16 wells was made by taking two well formers from a Galileo 80-1214-C16-1.5 comb and a 0.75 mm thick piece of plastic (FIG. 19A) and clamping them together with binder clamps.

The comb assembly was placed in a casting tray for a Galileo 80-1214 gel box, and 80 grams of agarose was added; after gelation, the combs were removed, and the gel was submerged in buffer (25 mM Tris Acetate, pH 7.5; 0.1 mM $Na_2EDTA$).

Figure 19B:
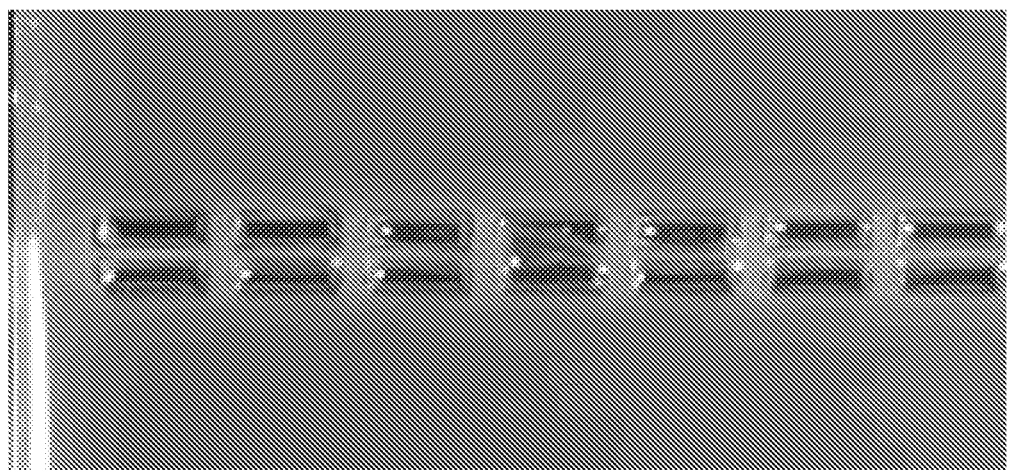
FIG. 19B shows the row of gels created by the comb according to some embodiments.

The resulting gel (FIG. 19B) has two sets of wells 0.75 mm apart.

The wells closest to the (+) electrode are the sample wells, and the wells closest to the (−) electrode are the reagent wells.

Preparation of White Blood Cells (WBCs) from goat whole blood:

Note: all steps at room temperature

To 12 mL whole blood (Goat with ACD anticoagulant, Lampire) 36 mL Red Blood Cell (RBC) lysis buffer (155 mM Ammonium Cl; 10 mM $NaHCO_3$; 1 mM $Na_2EDTA$) was added. The solution was rocked for 3 minutes and white cells pelleted by centrifugation 400×g 4 minutes.

The pink supernatant was decanted, and the red pellet resuspended by vortexing in 25 mL of RBC lysis buffer; after a second spin and decantation, the pink pellet was resuspended in 900 uL RBC lysis buffer.

Measurement of WBC DNA Concentration by Qubit:

A Qubit HS assay (Life Technologies) was used.

Figure 20A:
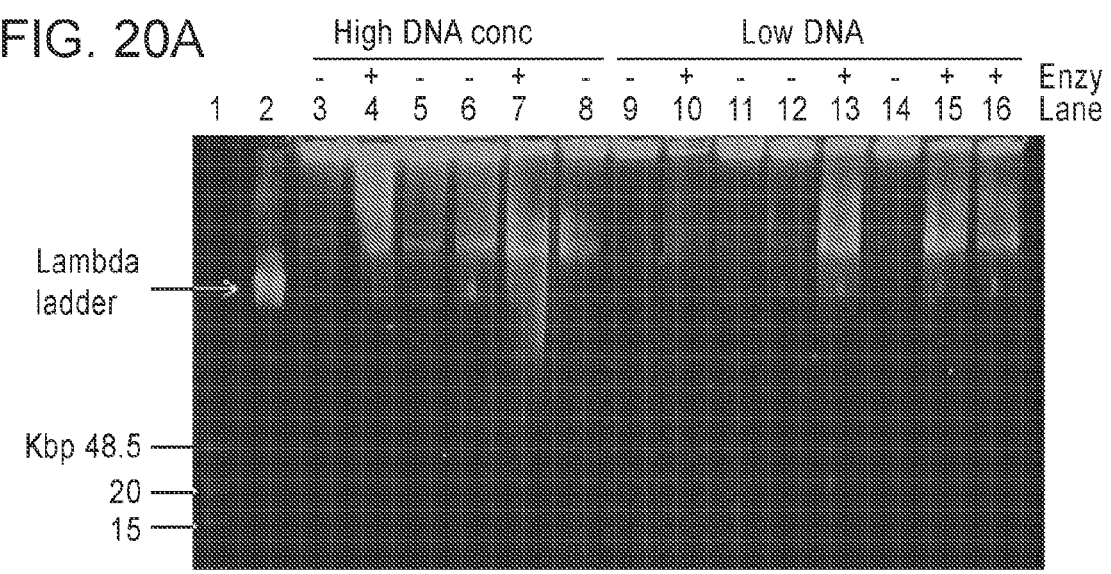
FIGS. 20A-B show transposase activity on DNA from white blood cells loaded in a gel according to some embodiments.

WBCs were lysed by mixing 40 uL of WBCs with 160 uL of TE/50 mM NaCl/1% SDS followed by incubation at 65° C. for 3 minutes. TE (800 uL) was added, and after vortexing to reduce viscosity, 1 or 2.5 uL of the DNA was added to 199 uL of Qubit reagent, per the vendor's protocol. Using this method, the concentration of DNA in the WBC solution was estimated to be 453 ng/uL Loading the Gel with WBCs and Lysis Solution:

To each reagent well in the agarose gel (FIG. 20A, B) 40 uL of lysis buffer (10 mM Tris-HCl, pH7.5, 1 mM EDTA, 3% SDS, 5% glycerol, 50 ug/mL each bromophenol blue and phenol red) was added High load WBC samples were prepared by mixing:

100 uL of isolated WBCs at 453 ng/ul in RBC lysis buffer.

300 uL of TBSEG (50 mM Tris-HCl, pH 7.6, 150 mM NaCl, 1 mM EDTA, 5% glycerol).

5 uL of a solution with 2 mg/mL each bromophenol blue and phenol red.

20 ul of the High-load WBC samples in TBSEG (equivalent to 2,000 ng of DNA) were loaded in sample wells 3-9.

Low-load WBC samples were prepared by mixing:

40 ul of isolated WBCs at 453 ng/ul in RBC lysis buffer.

300 uL of TBSEG.

5 uL of a solution with 2 mg/mL each bromophenol blue and phenol red.

17 ul of the Low-load WBC samples in TBSEG (equivalent to 800 ng DNA per well) were loaded in sample wells 9-16.

To extract and purify the WBC DNA, the gel was run for 74 minutes @100V DC.

In-well processing of electrophoretically extracted DNA with adapter-loaded mutant Tn5 transposase:

The gel was removed from the tank; excess buffer was poured off, and the gel was placed on a flat plastic surface.

To all 32 wells, 40 uL of Transposase Buffer (TB, 25 mM Tris Ac pH 7.5; 20 mM MnCl) was added.

1 mL of a modified transposase buffer (mTB) was prepared:

| Reagent | Final concentration |
|---|---|
| 735 uL H2O | na |
| 25 uL 1M TrisAc pH 7.5 | 25 mM |
| 170 uL 117 mM MnCl | 20 mM |
| 50 uL Glycerol | 5% |
| 10 uL dye, 2 mg/mL BPB and Phenol Red | 20 ug/mL |
| 10 uL of 100 mg/mL Hydroxypropyl cyclodextrin (Acros, catalog # 297560250) | 1 mg/ml |

As shown in the table below, sample wells were filled with 40 uL of modified transposase buffer, or 40 uL of 1×HMW buffer (Kapa Biosystems; 1×HMW buffer is 25 mM Tris Acetate pH7.5; 15% DMSO) or 25 uL of mTB or 1×HMW+mutant Tn5 transposase pre-loaded with synthetic duplex DNA adapters (Kapa Biosystems):

The table below shows what was loaded into the sample wells for the enzymatic digestion step.

TB is transposase buffer; all wells were filled with this buffer. Wells that received TB buffer only, with no subsequent additions, are labeled "TB".

After adding the TB buffer to all wells, some wells, marked "mTB" or "HMW", received modified transposase buffer or HMW buffer containing a mutant Tn5 transposase (lanes marked "TnP", 180 ng/ul, Kapa Biosystems). Prior to loading, the transposase had been preincubated with double-stranded sequencing adapters carrying transposase binding sites to generate fully loaded transposasomes, which are competent for in vitro transposition of the adapters into white cell HMW DNA targets.

| Sample Well | ng WBC DNA | Buffer | TnP, uL |
|---|---|---|---|
| 1 | 0 | TB | 0 |
| 2 | 0 | TB | 0 |
| 3 | 2,000 | mTB | 0 |
| 4 | 2,000 | mTB | 4 |
| 5 | 2,000 | TB | 0 |
| 6 | 2,000 | HMW | 0 |
| 7 | 2,000 | HMW | 4 |
| 8 | 2,000 | TB | 0 |
| 9 | 800 | mTB | 0 |
| 10 | 800 | mTB | 4 |
| 11 | 800 | TB | 0 |
| 12 | 800 | HMW | 0 |
| 13 | 800 | HMW | 4 |
| 14 | 800 | TB | 0 |
| 15 | 800 | HMW | 2 |
| 16 | 800 | HMW | 0.8 |

Sample Well Loading

The loaded gel was incubated for one hour at room temperature.

Standards were added to the sample wells in lanes 1 and 2 (lane 1, 5 uL of NEB 1 kb extend ladder (catalog # N3239S); lane 2, a slice of NEB lambda ladder (catalog # N03405).

The gel was run for 30V for 30 minutes and then 100V for 90 minutes, and then stained with Ethidium Bromide and photographed with UV transllumination.

Results: Transposase Activity on DNA from WBCs Loaded in a Gel

Results are shown in FIG. 20. Comparing lanes 12 and 14 (800 ng DNA/lane, no transposase) to lanes 13, 15, and 16 (800 ng DNA/lane, with transposase) we see there is a dose dependent cleavage of DNA; without transposase, the DNA remains in the wall of the sample well indicating that it is too large to enter the gel. With transposase addition, a digested DNA band with an apparent mobility of greater than several hundred kbp is seen. This is expected since mutant Tn5 transposasomes loaded with synthetic adapters have been demonstrated to readily react with HMW DNA, fragmenting the HMW target DNA upon insertion of the synthetic adapters.

Figure 20B:
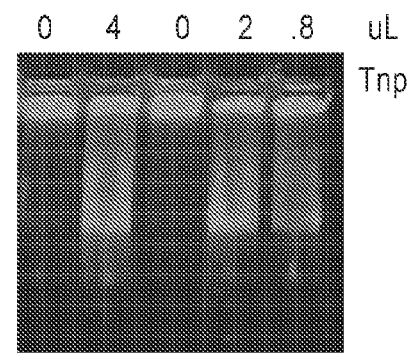

(FIG. 20B shows the same lanes as in FIG. 20A 12-16, except relabeled to clearly show the amount of transposase used in each lane.)

This demonstrates that the purified HMW DNA that was trapped on the wall of the well is accessible and readily modified by enzymatic reagents that can be loaded into the sample well following electrophoretic purification. This also demonstrates compatibility with standard NGS library preparation workflows that utilize transposase-mediated adapter addition and fragmentation reactions.

Example: Rapid Electrophoretic Workflow for Production of Pacific Biosciences SMRTbell™ Sequencing Libraries Directly from Mammalian White Blood Cells A cassette of the type shown in FIG. 15C containing a 0.75% agarose in 0.5×KBB buffer was used. The total volumes of the reagent and sample wells were 350 and 90 ul, respectively.

Goat WBCs were prepared from whole blood by selective lysis of the RBCs as described in the previous example (see, e.g., paras. 127-133).

Purified goat WBCs (containing 12 ug of genomic DNA) were loaded into the empty sample well of the cassette in RBC lysis buffer (see, e.g., para. 136). Total volume of the loaded sample was 80 ul. Lysis buffer (see, e.g., para. 135), 320 ul, was added to the empty reagent well. Cell lysis and DNA purification was carried out by electrophoresis in a SageELF instrument (Sage Science, Inc.) using the separation electrodes at 100V for 40 minutes.

After purification electrophoresis, the reagent and sample wells were emptied. The reagent well was reloaded with 320 ul of Tris-HCl, pH 8.0, 10 mM $MnCl_2$. The sample well was reloaded with the same buffer containing 0.72 ug of mutant Tn5 transposase (Kapa Biosystems), that had been pre-loaded with a hairpin adapter that carries the Tn5 transposase recognition sequence in the duplex region, and also carries the PacBio sequencing primer binding site in the single-stranded loop of the hairpin:

5'CTGTCTCTTATACACATCTTTTTCCTCCTCCTCCGTTGTTGTTGTTA
GATGTGTATAAGAGACAG3'/

The cassette was incubated at 37 C for 30 minutes to allow the transposition reaction with the immobilized goat genomic DNA.

After transposition, the reagent and sample wells were emptied, the reagent well was refilled with 50 mM Tris-HCl, pH 8.0, 10 mM $MgCl_2$. The sample well was filled with 70 ul of the same buffer additionally containing 0.1 mM each dATP, dTTP, dCTP, dGTP, 0.06 mM NAD+, 3 units T4 DNA polymerase (New England Biolabs), and 10 units E. coli DNA ligase. The cassette was incubated at 37 C for 30 minutes to allow gap filling and nick ligation of the gaps created by transposition of the SMRTbell™ hairpin adapters into the goat genomic DNA.

After gap closure, 400 ng of trypsin was added to the sample well in 3 ul in order to inactivate the T4 polymerase and ligase. The contents of the sample well were mixed by pipetting and the cassette was incubated for 30 minutes at 37 C. To terminate the trypsin digestion, 1 ug of soybean trypsin inhibitor was added in a 1 ul volume. The contents of the sample well were mixed by pipetting and the cassette was incubated for an additional 15 minutes at 37 C.

To remove, unreacted adapters, and unreacted goat genomic DNA, 30 units of T5 exonuclease (New England Biolabs) was added to the sample well (in a 3 ul volume), and the sample well contents were mixed by pipetting. Exonuclease digestion was carried out for 30 minutes at 37 C.

After exonuclease digestion, the reagent well was emptied and refilled with lysis buffer. The cassette was electrophoresed in separation mode in a SageELF instrument using continuous 60V electophoretic field for 1 hour, followed by a 2 hour period of pulsed field electrophoresis using the waveform for resolving 5-430 kb DNA, described in the Pippin Pulse User Manual (http://www.sagescience.com/product-support/pippin-pulse-support/). After separation electrophoresis, electroelution is carried out in the ELF instrument for 45 minutes using a voltage of 50V. At the end of elution, a 25V field is applied in the reverse direction for 5 seconds to help release the eluted DNA from the ultrafiltration membrane of the elution modules. The finished SMRTbell™ libraries are recovered from the elution modules in electrophoresis buffer.

Any and all references to publications or other documents, including but not limited to, patents, patent applications, articles, webpages, books, etc., presented anywhere in the present application, are herein incorporated by reference in their entirety.

Although a few variations have been described in detail above, other modifications are possible. For example, any logic flows depicted in the accompanying figures and/or described herein do not require the particular order shown, or sequential order, to achieve desirable results. Other implementations may be within the scope of at least some of the following exemplary claims.

As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and apparatuses/devices which may further include any and all elements from any other disclosed methods, systems, and devices, including any and all elements corresponding to isolating nucleic acid from a biological sample (e.g., containing nucleic acid and non-nucleic acid elements). For example, in some embodiments systems, devices and methods. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Also, some embodiments correspond to systems, devices and methods which specifically lack one and/or another element, structure, and/or steps (as applicable), as compared to teachings of the prior art, and therefore represent patentable subject matter and are distinguishable therefrom (i.e. claims directed to such embodiments may contain negative limitations to note the lack of one or more features prior art teachings).

When describing the nucleic acid processing, terms such as linked, bound, connect, attach, interact, and so forth should be understood as referring to linkages that result in the joining of the elements being referred to, whether such joining is permanent or potentially reversible. These terms should not be read as requiring the formation of covalent bonds, although covalent-type bond might be formed.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed:

1. An electrophoresis system, comprising:
an electrophoresis gel matrix having a first end, a second end, a length, a width, a first lengthwise side and a second lengthwise side;
a reagent well containing a lysis reagent configured within the electrophoresis gel matrix portion proximate the first end;
a sample well containing a sample of biological cells and configured within the electrophoresis gel matrix proximate the first end and between the reagent well and the second end;
a first negative electrode of a pair of electrophoretic electrodes arranged at the first end;
a first positive electrode of the pair of electrophoretic electrodes arranged at the second end; and
wherein:
upon application of a first biasing voltage across the pair of electrophoretic electrodes, reagent is driven from the reagent well into and/or through the sample well.

2. The electrophoresis system of claim 1, wherein the sample well includes a cell suspension.

3. The electrophoresis system of claim 1, wherein the lysis reagent is a negatively charged lysis reagent.

4. The electrophoresis system of claim 3, wherein upon application of the first biasing voltage, the negatively charged lysis reagent is driven into a sample well including a cell suspension to produce DNA molecules of the cells contained in the cell suspension.

5. The electrophoresis system of claim 4, wherein the produced DNA molecules are configured on at least one side of the sample well.

6. The electrophoresis system of claim 5, wherein upon application of a second biasing voltage across the pair of electrophoretic electrodes, the accumulated DNA electrophoreses out of the sample well.

7. The electrophoresis system of claim 6, further comprising:
a plurality of elution receiving areas or channels arranged along the first lengthwise side of the gel, each receiving area having a first side arranged adjacent the first lengthwise side of the gel and second side spaced apart from the first side of the receiving area; and
a plurality of pairs of elution electrodes corresponding to each elution receiving channel, wherein a first negative elution electrode of a first pair of elution electrodes is arranged proximate the second lengthwise side of the gel across from the first side of a first elution receiving channel and a first positive elution electrode of the first pair arranged proximate to the second side of the first elution receiving channel;
wherein
upon application of the second biasing voltage, DNA fragments of the electrophoresed DNA accumulate proximate one and/or another of the elution receiving channels; and
upon application of a biasing voltage across one and/or another of the pairs of elution electrodes, the DNA fragments are driven into one and/or another of respective elution channels.

8. An electrophoresis method comprising:
providing the system of claim 1;
loading a cell suspension comprising the sample of biological cells into the sample well;
loading the reagent into the reagent well;
applying a first voltage bias across the pair of electrophoretic electrodes, wherein application of the first voltage bias causes the reagent to move from the reagent well to the sample well,
wherein
the reagent is configured to cause the cells in the suspension to lyse, and
DNA molecules from the cells accumulate on at least one side of the sample well.

9. The method of claim 8, further comprising incubating the cell suspension within the sample well.

10. The method of claim 8, further comprising breaking down the DNA molecules into fragments.

11. The method of claim 8, wherein:
the system further comprises a plurality of elution receiving areas or channels arranged along the first lengthwise side of the gel, each receiving area having a first side arranged adjacent the first lengthwise side of the gel and second side spaced apart from the first side of the receiving area, and
the method further comprises electrophoretically driving the DNA fragments from the sample well to the plurality of elution channels.

12. The method of claim 9, wherein incubation comprises:
adding a first additive to the sample well and incubating with the contents of the sample well the cells therein; and/or
adding a second additive to the sample well and incubating with the cells therein; and/or
adding a third additive to the sample well and incubating with the cells therein.

13. The method of claim 12, wherein the first additive, the second additive, and the third additive, and corresponding incubations thereof, are performed sequentially.

14. The method of claim 12, wherein:
the first additive comprises at least one adapter;
the second additive is T4 DNA polymerase, dNTPs, *E. coli* ligase, and nicotinamide adenine dinucleotide; and
the third additive is Exonuclease T5.

15. The method of claim 12, wherein the first additive comprises a transposase assembled with oligonucleotides comprising a first portion which has at least one transposase recognition region and a second portion which has a sequencing library adapter region.

* * * * *